US012751735B2

(12) United States Patent
Vyas et al.

(10) Patent No.: US 12,751,735 B2
(45) Date of Patent: Oct. 6, 2026

(54) HYDRO DISSECTION AND SUCTION LAPAROSCOPIC INSTRUMENTS AND METHODS OF USE

(71) Applicants: Dinesh Vyas, Elk Grove, CA (US); Jeffrey J. Christian, Morgan Hill, CA (US)

(72) Inventors: Dinesh Vyas, Elk Grove, CA (US); Jeffrey J. Christian, Morgan Hill, CA (US)

(73) Assignee: Dinesh Vyas, Elk Grove, CA (US)

( * ) Notice: Subject to any disclaimer, the term of this patent is extended or adjusted under 35 U.S.C. 154(b) by 0 days.

(21) Appl. No.: 18/378,354

(22) Filed: Oct. 10, 2023

(65) Prior Publication Data

US 2024/0180582 A1 Jun. 6, 2024

Related U.S. Application Data

(63) Continuation-in-part of application No. 18/089,368, filed on Dec. 27, 2022.

(Continued)

(51) Int. Cl.

*A61B 17/3203* (2006.01)
*A61B 17/295* (2006.01)

(Continued)

(52) U.S. Cl.

CPC ...... *A61B 17/3203* (2013.01); *A61B 17/3421* (2013.01); *A61B 18/1445* (2013.01);

(Continued)

(58) Field of Classification Search

CPC ............ A61B 17/3203; A61B 17/3421; A61B 18/1445; A61B 34/35; A61B 17/295; A61B 2017/00411; A61B 2017/320044; A61B 2017/3445; A61B 2018/00595; A61B 2217/005; A61B 2217/007

See application file for complete search history.

(56) References Cited

U.S. PATENT DOCUMENTS

2011/0313286 A1* 12/2011 Whayne ............... A61B 18/148 600/431
2019/0328451 A1* 10/2019 Smith ................ A61B 18/1477

(Continued)

*Primary Examiner* — Kathleen S Holwerda
*Assistant Examiner* — James R McGinnity
(74) *Attorney, Agent, or Firm* — William A. English; Vista IP Law Group LLP

(57) ABSTRACT

A laparoscopic instrument includes fluid carrying channels incorporated into lateral aspects of jaws of the instrument and extending to outlets adjacent distal tips of the jaws, fluid carrying channels incorporated into a shaft of the instrument, and flexible fluid carrying channels connecting the distal ends of the shaft channels with the proximal end of respective jaw channels. An actuator on the device handle controls either delivery of fluid jets emanating lateral to tissue grasped between the instrument jaws or suction from the distal tips of the jaws to remove fluid in the vicinity of the jaws. The fluid jets perform atraumatic tissue dissection lateral to the structures grasped by the jaws, while the grasping jaws provide counter traction while conducting soft tissue hydro-dissection, by stabilizing the tissue in a direction opposite to the force exerted by the hydro-dissection fluid jets.

12 Claims, 20 Drawing Sheets

Related U.S. Application Data

(60) Provisional application No. 63/421,511, filed on Nov. 1, 2022, provisional application No. 63/312,770, filed on Feb. 22, 2022.

(51) Int. Cl.

| | |
|---|---|
| ***A61B 17/34*** | (2006.01) |
| ***A61B 18/14*** | (2006.01) |
| ***A61B 34/35*** | (2016.01) |
| *A61B 17/00* | (2006.01) |
| *A61B 17/32* | (2006.01) |
| *A61B 18/00* | (2006.01) |

(52) U.S. Cl.

CPC ..... *A61B 34/35* (2016.02); *A61B 2017/00411* (2013.01); *A61B 17/295* (2013.01); *A61B 2017/320044* (2013.01); *A61B 2017/3445* (2013.01); *A61B 2018/00595* (2013.01); *A61B 2217/005* (2013.01); *A61B 2217/007* (2013.01)

(56) References Cited

U.S. PATENT DOCUMENTS

| | | | | |
|---|---|---|---|---|
| 2020/0315652 | A1* | 10/2020 | Vetter .................. | A61B 5/0036 |
| 2020/0405380 | A1* | 12/2020 | McHenry ........... | A61B 18/1206 |
| 2025/0040793 | A1* | 2/2025 | Hassidov ............... | A61B 8/445 |

* cited by examiner

FIG. 6c
View B-B
FIG. 6b
Section A-A
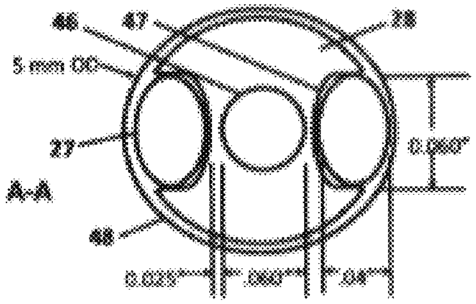
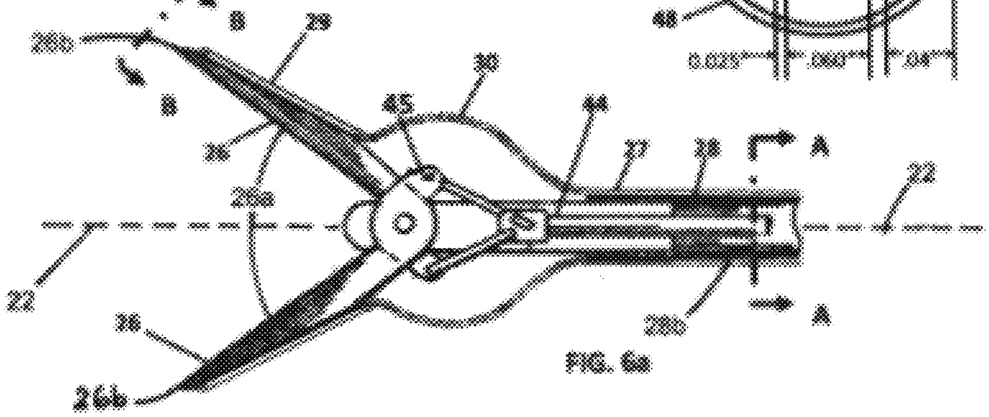
FIG. 6a
FIG. 7a
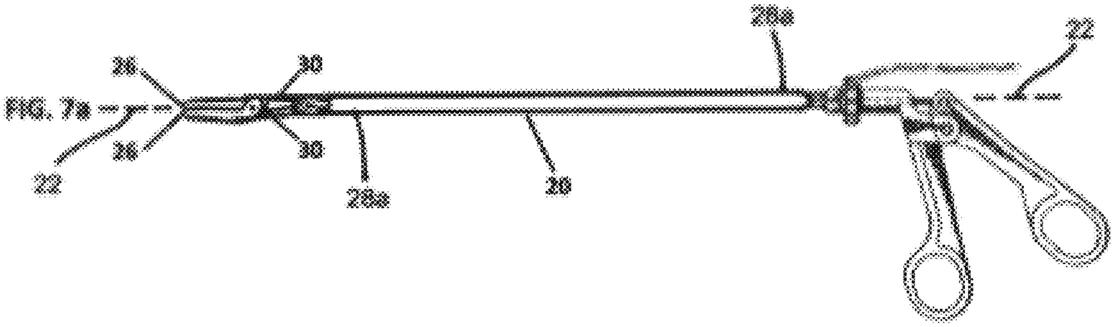
FIG. 7b
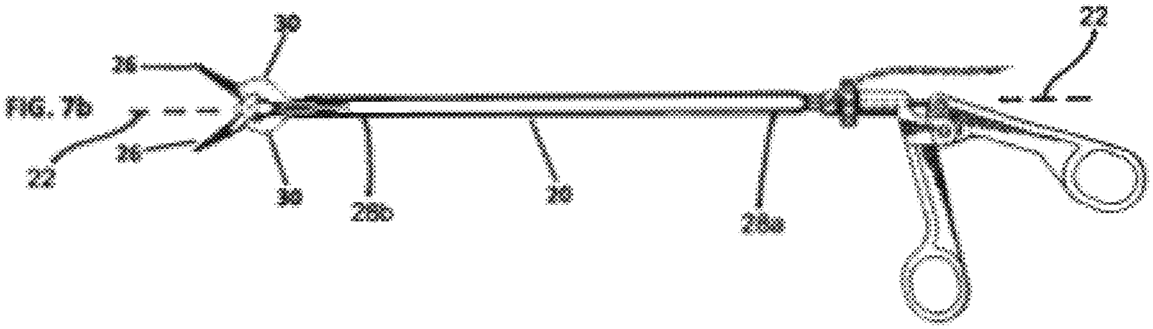

FIG. 12

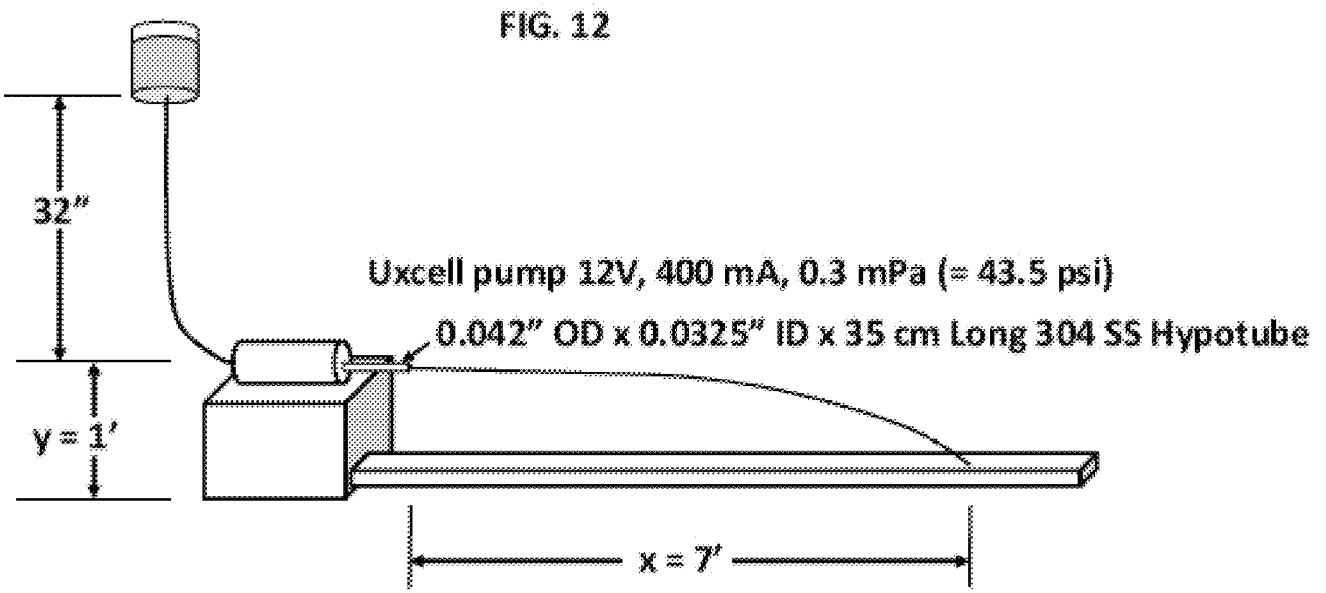

Water Jet Velocity Calculation $D_y = 0.5gt^2$ where g = 32.17 ft/sec$^2$ For $D_y$ = 1', t = 0.25 sec $D_x = Vt$ For Dx = 7' at t = 0.25 sec, Velocity of jet stream V = 28 ft/sec (= 8.53 m/sec)

V = 16.66 m/sec for cataracts (Tas A. Minimal water-jet hydrodissection. Clinical Ophthalmology 2018;12:1-5)

Flow Rate: 0.032" ID = 0.08 cm CS Area = $\pi r^2$ = 3.14(.08)$^2$ = .02 cm$^2$ V = 8.53 m/sec = 853 cm/sec CS Area x Velocity = .02 cm$^2$ x 853 cm/sec = 4.29 cc/sec 4.29 cc/sec x 60 sec/min = .26 L/min FIG. 17c
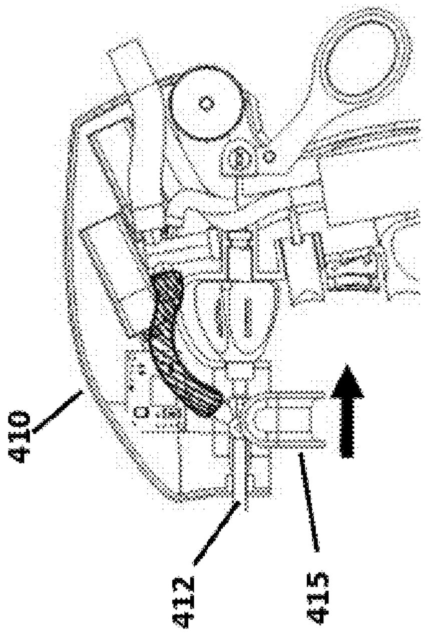
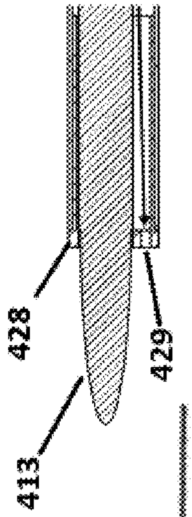
FIG. 17e
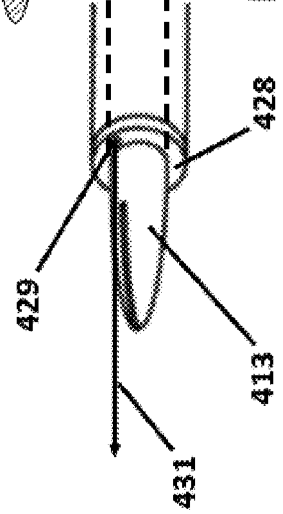
FIG. 17d
FIG. 17a
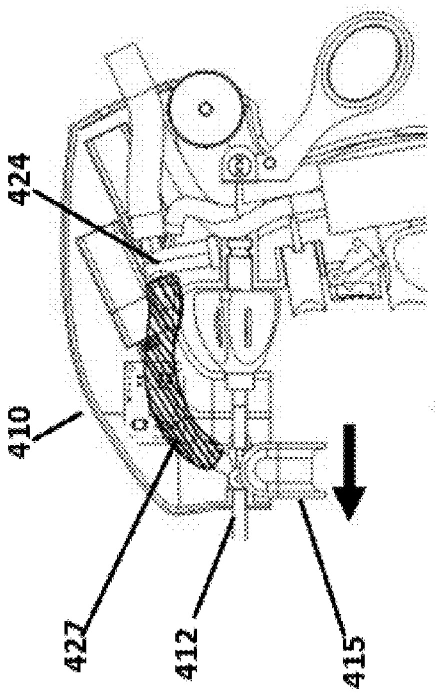
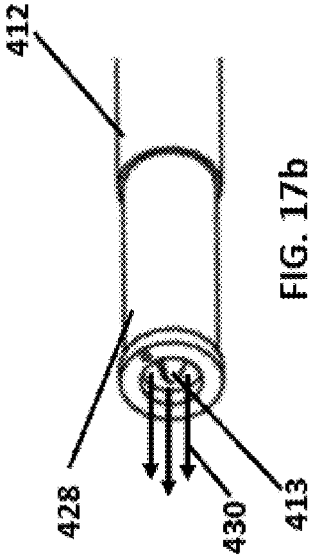
FIG. 17b

HYDRO DISSECTION AND SUCTION LAPAROSCOPIC INSTRUMENTS AND METHODS OF USE

RELATED APPLICATION DATA

The present application claims benefit of U.S. provisional application Ser. No. 63/421,511, filed Nov. 1, 2022, and is a continuation-in-part of co-pending U.S. application Ser. No. 18/089,368, filed Dec. 27, 2022, which claims benefit of U.S. provisional application Ser. No. 63/312,770, filed Feb. 22, 2022, and 63/421,511, filed Nov. 1, 2022, the entire disclosures of which are expressly incorporated by reference herein the entire disclosure of which is expressly incorporated by reference herein.

TECHNICAL FIELD

The present application relates to surgical devices and systems and, more particularly, to devices and methods for tissue dissection, e.g., conducted in laparoscopic surgery, which may involve blunt tissue dissection performed via a focused fluid jet instead of the mechanical tissue disruption typically performed by laparoscopic dissectors and graspers. For example, the devices and systems herein may include a laparoscopic instrument that includes modes of mechanical tissue dissection, hydro dissection, suction, and irrigation provided in a single instrument.

BACKGROUND

In laparoscopic, thoracic, gynecological, urological, and minimally invasive surgery, such as robotic surgical procedures, isolation of anatomic structures, such as blood vessels and ducts, are performed via blunt dissection maneuvers involving spreading and tearing of soft tissue adjacent to the vessels and ducts. If the organ involved in the surgery is ischemic or necrotic, the organ and surrounding soft tissue becomes swollen and edematous, making it impossible to discern the outlines and locations of underlying ducts and vessels. Surgical maneuvers with existing laparoscopic graspers and dissectors carry significant potential of disrupting unrecognized organs, ducts, and vessels, which may lead to spillage of toxic infective contents into the abdominal cavity and hemorrhage.

Blunt dissection of soft tissue during laparoscopic surgery may be hazardous when the tissue is swollen and edematous, and the outline of blood vessels and ducts coursing through the soft tissue is not visible via endoscopic observation. In gangrenous cholecystitis, the gallbladder is distended to such a degree that it becomes ischemic, with compromise to its blood supply. Necrosis of the organ occurs, and the resultant inflammation and tissue swelling in the area of the gallbladder obscures the location of the cystic duct and the cystic artery. These structures must be surgically isolated, ligated or clipped, and transected for gallbladder removal. Mechanical dissection of the gangrenous gallbladder with traditional laparoscopic instruments, such as Maryland dissectors, may easily cause transection or laceration of non-visualized common bile duct, portal vein, colon, other intestines, cystic duct, and cystic artery, causing spillage of infected bile in the abdominal cavity and hemorrhage.

Other endoscopic procedures requiring execution of difficult and hazardous surgical blunt dissection include intra-abdominal endometriosis lesion resection, adhesiolysis or lysis of adhesions, and video assisted thoracic surgery or VATS, generally involving lung resection procedures and drainage of empyema.

Previous laparoscopic forceps exist that supply fluid irrigation and suction to the jaws of the instruments. One such instrument, described by Fischer in U.S. Pat. No. 9,308,014, teaches the use of a fluid jet at or in a stationary jaw of a forceps to dissect tissue.

Therefore, improved devices and methods for performing dissection of tissue within a patient's body would be useful.

SUMMARY

The present application relates generally to surgical devices and systems, and, more particularly, to devices for tissue dissection, e.g., conducted in laparoscopic and/or robotic surgery, and to systems and methods for using such devices. The devices may include surgical instruments, e.g., a laparoscopic grasper, forceps, scissors, clip applier, vessel sealer, the like, that provide multiple modes of operation, e.g., hydro dissection, suction, and/or irrigation in addition to other optional mechanical functionalities, e.g., including end effectors for mechanical tissue dissection, cutting, and the like, provided in a single instrument. The devices may be provided in systems that include other components for operating the devices, e.g., sources or fluid and/or vacuum, electrical power sources, and the like. The devices may also be included in robotic surgical systems that may be operated remotely.

Optionally, the devices and systems may include one or more additional components or functionalities. For example, the devices may include one or more sensors on or adjacent their end effectors, e.g., Doppler or other sensors for identifying blood flow in contacted tissue, microfluidics sensors for identifying tissue characteristics and the like, one or more electrodes or other cautery elements, vessel sealing elements, and/or one or more imaging Clements. One or more processors or controllers may be coupled to these elements, e.g., to analyze signals from sensors, generate images on a display, and the like. If one or more imaging elements are provided on the devices, a display may be provided, e.g., mounted on a proximal end of the devices or remotely from the devices, which may allow visual monitoring of a surgical field during use of the devices.

In accordance with one example, an instrument, e.g., a laparoscopic grasper or forceps, is provided that includes double action jaws that include rigid nozzles on lateral aspects of each jaw. Fluid-carrying channels extend along lateral aspects of the instrument shaft, and a length of flexible hose connects the distal end of each channel to a proximal end of a respective jaw nozzle channel. The short flexible hose sections may adopt a substantially straightened position when the jaws are closed, such that their outer profile does not exceed the outer profile of the instrument shaft, allowing the instrument to be inserted through a trocar, e.g., a five millimeter (5 mm) laparoscopic trocar.

In another example, a laparoscopic forceps is provided that includes multiple modes of operation, e.g., including two or more of mechanical tissue dissection, hydro dissection, suction and irrigation, cautery, vessel sealing, and microfluidics provided in a single instrument. Alternatively, other surgical instruments may be provided that include these modes of operation, e.g., a bowel grasper, clip applier, scissors, vessel sealer, and the like. Tissue manipulation and blunt tissue dissection may be conducted with jaws of the forceps extended distal to a tip of a coaxial sheath. Tissue hydro dissection may also be performed in this configuration, with the forceps grasping tissue to provide counter-traction while a high velocity fluid jet performs atraumatic surgical dissection without the mechanical tissue disruption typically performed by conventional laparoscopic dissectors and graspers. Hydro dissection may safely isolate and/or dissect ducts, blood vessels and other anatomic structures during surgical procedures in gangrenous or edematous tissue and organs. The forceps may be retracted fully into the sheath, e.g., to perform suctioning and/or to perform pure hydro dissection without applying tissue counter-traction. Suction may clear hydro dissection fluid and/or blood from the surgical field, and fluid irrigation may clear the suction cannula of clogging due to tissue debris and blood clots. Optionally, the instrument may include a self-contained battery-operated fluid pump and a port that allows device connection to a vacuum cannister in the operating room.

In yet another example, a hydro dissection and suction laparoscopic forceps device is provided that includes two movable jaws connected to distal end of a long rigid, e.g., five millimeter (5 mm) outer diameter, shaft, with the jaws configured to be opened and closed by an actuator on a handle on a proximal end of the shaft, e.g., including an elongated stationary ring that accommodates multiple fingers and a movable thumb ring that actuates the jaws. Tubular channels may be provided on lateral aspects of the shaft and jaws, e.g., including a pair of shaft channels extending between the proximal and distal ends of the shaft and a relatively short, e.g., three millimeter (3 mm) long, tubular jaw channel on each of the jaws, which are circumferentially exposed to allow attachment of two flexible tubes connecting each shaft channel to a corresponding jaw channel in a fluid tight fashion. The flexible tubes may allow the closed jaw instrument to maintain a desired maximum outer diameter or other profile, e.g., a five millimeter (5 mm) outer diameter throughout the length of the device, e.g., for insertion through a corresponding, e.g., five millimeter (5 mm), inner diameter trocar or sheath.

Once the jaws are disposed inside an abdominal cavity of a patient, the jaws may be opened and closed while the flexible tubes allow fluid delivery lateral to the jaws for atraumatic hydro-dissection of tissue lateral to anatomic structures grasped by the jaws, e.g., as counter traction is applied to the tissue stabilized by the forceps. Such a method of lateral tissue hydro-dissection while applying centralized tissue counter traction may be less traumatic to tissue than conventional blunt dissection with conventional laparoscopic forceps, as the such conventional forceps typically involve tissue puncture and tissue tearing as components of mechanical blunt dissection. In contrast, hydro-dissection, as enabled by the devices and methods herein, uses gentle fluid jet streams to separate tissue and isolate anatomic structures, eliminating the sharp force tissue interaction associated with mechanical blunt dissection.

In some laparoscopic procedures, it may be desirable to perform surgery with forceps containing double action jaws rather than a single action jaw and a stationary jaw. Double action jaws may permit a wider grasp of tissue to prevent slippage during tissue manipulation. Double action jaws may also enable the jaws to remain in axial orientation with the shaft of the instrument, with the jaws opening symmetrically on either side of the shaft. Application of the laparoscopic forceps with double action jaws may be more intuitive, facilitating efficient surgical technique and saving operative time. In contrast, with a single action forceps, the instrument shaft needs to be displaced to the side of the stationary jaw to accurately grasp tissue as intended. Thus, double action jaws on the device may be particularly useful, although, alternatively, single action jaws may also be provided, if desired.

In one example, the hydro-dissection laparoscopic forceps devices provided herein may incorporate a self-contained fluid pump and/or a battery or other power source to power the pump, e.g., within or on the handle device. Saline may be supplied to the pump via an intravenous line, e.g., attached to a hanging intravenous fluid bag. Optionally, a separate hose supplying wall suction in the operating room is also connected to the device handle.

In one example, the device may include two normally-closed valves coupled to respective actuators, e.g., which reside in series in the intravenous line attached to both tubular channels on the proximal end of the shaft. For example, a first trumpet valve may control both the electrical supply to the fluid pump and the fluid flow lateral to the forceps jaws, and a second trumpet valve may activate vacuum to clear fluid injected during hydro dissection.

Optionally, the laparoscopic hydro dissection forceps and/or other devices described herein, e.g., including fluid pump and battery, may be a single-use device that is disposed following the surgical procedure, to avoid the need for device cleaning, re-sterilization, and storage between successive procedures. Alternatively, all or some components of the device may be reusable, e.g., after cleaning and/or sterilization.

In one example, the fluid carrying tubular channels located on the grasper jaws may have a smaller inner diameter than the tubular channels located on the lateral aspects of the instrument shaft. This allows the velocity of the fluid jet emanating from the grasper jaw channels to be tuned to a desired level, e.g., based on pressure and/or flow rate specifications generated by the fluid pump.

Pathologic conditions may exist that cause anatomic landmarks to be obscured during endoscopic surgery, rendering tissue dissection difficult and hazardous. For example, in laparoscopic cholecystectomy or removal of the gallbladder, surgical dissection must be performed to isolate the cystic artery and cystic duct to allow for their ligation and transection prior to gallbladder removal. Acute cholecystitis is inflammation of the gallbladder caused by occlusion of the cystic duct by gallstones. The gallbladder becomes distended, and the pressure inside the organ may increase to such a level that it compromises the blood supply and causes ischemia, leading to gangrenous cholecystitis, which occurs in over 20% of acute cholecystitis cases. The severe inflammation observed in gangrenous cholecystitis causes such a degree of swelling and edema in the gallbladder and surrounding tissues that the outlines of anatomic structures, such as the cystic duct and cystic artery are invisible under laparoscopic visualization, and normally observed outlines and landmarks are obscured.

Blunt tissue dissection using conventional laparoscopic forceps requires insertion of the closed tips of the forceps jaws into tissue without perceptible landmarks, followed by opening of the jaws to spread apart the tissue. The tissue disruption associated with this blunt dissection maneuver may easily lacerate or transect unseen vessels and ducts. In contrast, hydro-dissection is a less traumatic approach to isolation of anatomic structures embedded in edematous tissue. Surgical dissection of inflamed tissue also prolongs procedure times, increasing the physical stress of surgery and general anesthesia to the patient, thus increasing the patient morbidity and mortality.

A modified technique of tissue dissection is proposed herein, involving tissue dissection performed solely by simultaneous hydro-dissection lateral to both sides of double action movable laparoscopic grasper jaws. The jaws of the devices described herein may not be applied in a typical fashion for mechanical tissue disruption and blunt dissection. Rather, the jaws may gently grasp and fixate exposed tissue prior to instillation of pressurized fluid jets lateral to the grasping jaws to perform hydro dissection of the soft tissue to achieve isolation of the desired anatomic structures.

The hydro dissection devices and methods herein may also be used in additional endoscopic procedures, e.g., to isolate delicate anatomic structures obscured by overlying amorphous tissue, such as resection of intra-abdominal endometriosis lesions, lysis of tissue and organ adhesions, and video assisted thoracic surgical procedures such as lung resection and lobectomy. In these procedures, dissection of connective tissue surrounding delicate organs, blood vessels and ducts may be performed less traumatically via hydro dissection versus standard mechanical blunt surgical dissection.

In accordance with one example, a device is provide for performing hydro-dissection of tissue within a patient's body that includes an elongate shaft comprising a proximal end, a distal end sized for introduction into the patient's body, and one or more shaft channels extending between the proximal and distal ends; first and second jaws on the distal end coupled to an actuator on the proximal end for moving the jaws between closed and opened positions, each jaw comprising a jaw channel comprising an outlet disposed adjacent a distal tip of the respective jaw; and a flexible tube extending between each jaw and the distal end of the shaft to fluidly couple the outlet of the respective jaw to the one or more shaft channels to deliver pressurized fluid from a fluid source through the one or more shaft channels, the flexible tubes, the jaw channels, and out the outlets to dissect tissue adjacent grasped between the jaws.

In accordance with another example, a device is provided for performing hydro-dissection of tissue within a patient's body that includes an elongate shaft comprising a proximal end, a distal end sized for introduction into the patient's body, and first and second shaft channels extending between the proximal and distal ends; first and second jaws on the distal end, each jaw comprising an outlet disposed adjacent a distal tip of the respective jaw; an actuator on the proximal end coupled to the jaws to manipulate the jaws between closed and opened positions; first and second flexible tubes extending between the jaws and the distal end of the shaft communicating between the outlet of the respective jaws and the first and second shaft channels, respectively; and a source of pressurized fluid coupled to the first and second shaft channels to deliver pressurized fluid through the shaft channels, the flexible tubes, the jaw channels, and out the outlets to dissect tissue adjacent grasped between the jaws.

In accordance with still another example, a method is provided for dissecting tissue within a patient's body that includes providing a dissection device comprising a distal end carrying a pair of jaws, each jaw comprising a nozzle adjacent a distal tip of the jaw; introducing the distal end into the patient's body with the jaws in a closed position; opening the jaws; manipulating the device and jaws to grasp tissue between the jaws; and delivering pressurized fluid out the nozzles to dissect tissue adjacent the jaws.

In accordance with another example, a combination hydro-dissection, irrigation, and suction laparoscopic forceps may be provided that includes a shaft, e.g., having about a three millimeter (3.0 mm) or smaller outer diameter, that resides and translates axially within a lumen of an outer sheath, e.g., a thin-walled sheath having an outer diameter of about five millimeters. The outer sheath may include a relatively large primary or central lumen and a relatively small (e.g., about 0.0325 inch (0.81 mm) inner diameter) fluid channel, e.g., incorporated in the wall the full length of the sheath, which may generate a high velocity hydro dissection jet emanating from a distal tip of the sheath. The central lumen of the sheath may be configured to supply either vacuum suction or low velocity fluid irrigation when connected to an appropriate source, as desired.

Optionally, a control valve integrated with an electrical switch may be provided that initiates fluid delivery by an attached fluid pump, with the capability to select either a high velocity jet emanating from the small diameter hydro dissection nozzle, or a low velocity fluid irrigation through the lumen of the outer sheath. Optionally, the control valve may include multiple settings, e.g., to allow different flow rates and/or volumes of fluid to be delivered, e.g., using a potentiometer and/or other control mechanism. A separate control valve produces suction through the outer sheath. In one example, an elastomeric seal maybe provided at a proximal end of the outer sheath, which may form a fluid-tight seal around the shaft of forceps while allowing the forceps to translate axially to expose the forceps jaws out of the distal end of the sheath or retract the jaws fully into the sheath.

The sheath may be constructed of a substantially rigid material, e.g., a thin-walled stainless steel tube of about 0.007 inch (0.18 mm) wall thickness, with about a 0.042 inch (1.05 mm) OD×0.0325 inch (0.81 mm) ID stainless steel tube welded or otherwise permanently axially along its inner surface to provide the fluid channel for the hydro dissection nozzle. Alternatively, the sheath may be a double lumen polymer extrusion with a small diameter, e.g., 0.0325 inch (0.81 mm), lumen incorporated in the wall of the extrusion. Exemplary materials for the extrusion may include one or more of Nylon, polyimide, polyetherether-ketone (PEEK), and the like. A fluid pump and power source that powers the pump, e.g., a nine-volt battery or cable connectable to an external power source, may be attached to the body of the forceps. Alternatively, the outer sheath, fluid pump, battery, and control valves may be incorporated into a frame that accepts and rigidly attaches to a conventional laparoscopic forceps.

In tests of a hydro dissection jet with fluid delivery supplied by a twelve-volt, 400 mA diaphragm pump powered by a nine-volt battery, the water jet exhibited a velocity of 28 m/sec. This fluid velocity is sufficient to dissect connective tissue without severing or lacerating blood vessels and ducts.

In robotic surgery, the limitation of a surgeon not working next to the patient creates major issues during instrument exchange. Instruments are introduced from a dependent area and may cause organs blocking the inner opening of the port. During exchanges, there are risks that the assistant surgeon can perforate an organ as the instruments always return to their initial position during removal of the previous instrument. Any of the devices and systems herein including a camera, microfluidics, and/or other sensors may warn the introducer of organ blocking the port and potential injury.

In accordance with another example, tissue manipulation and blunt tissue dissection are conducted with the jaws of the laparoscopic forceps exposed distal to the tip of a retracted coaxial outer sheath. With the instrument in this configuration, the shaft of the laparoscopic dissector forceps occupies the central lumen of the bushing located at the distal tip of the outer sheath of the device, forcing all fluid flow to exit a small diameter nozzle in the bushing to create a high velocity fluid jet. Tissue hydro dissection is performed in this configuration, with the forceps grasping tissue to provide counter-traction while the high velocity fluid jet performs atraumatic surgical dissection without the mechanical tissue disruption typically performed by laparoscopic dissectors and graspers. Hydro dissection safely isolates and dissects ducts, blood vessels and other anatomic structures during surgical procedures in gangrenous or edematous tissue and organs.

The outer sheath of the instrument may be extended to cover the jaws of the laparoscopic dissection forceps. As the cross-sectional area of the tapered forceps jaws is less than the cross-sectional area of the forceps shaft, an enlarged fluid path is formed at the tip of the outer sheath to enable suctioning, or to provide low velocity fluid irrigation. Suction clears hydro dissection fluid and blood from the surgical field, and fluid irrigation clears the suction cannula of clogging due to tissue debris and blood clots.

In one example, the instrument has a self-contained battery-operated fluid pump and a port that allows device connection to a vacuum cannister in the operating room.

In accordance with a particular example, a hydro dissection, irrigation, and suction laparoscopic forceps is provided that includes a three millimeter (3 mm) outer diameter or smaller laparoscopic forceps that resides inside a thin walled five millimeter (5 mm) outer sheath. The outer sheath extends nearly the full length of the shaft of the forceps, and is configured to translate axially along the forceps shaft to either fully expose or fully enclose the forceps jaws. Axial translation of the outer sheath is performed via an actuator located on the proximal handle of the device.

A bushing is attached to the distal tip of the outer sheath. In one example, the bushing is approximately twelve millimeters (12 mm) long, and includes a lumen approximately four millimeters (4 mm) in inner diameter therethrough. A one millimeter (1 mm) thick end cap on the bushing includes a central lumen with an inner diameter that is a sliding fit with the outer diameter of the laparoscopic forceps, and a tiny offset lumen approximately 0.3 millimeter in diameter.

When the outer sheath is fully retracted, the central lumen of the end cap on the bushing seals against the outer surface of the dissector forceps shaft, and all fluid flow exits the 0.3 mm diameter lumen, forming a high velocity fluid jet. When the outer sheath is fully extended to enclose the forceps jaws, injected fluid flows through a low resistance path, with ample clearance between the dissector forceps shaft and the inner surface of the outer sheath, and between the outer surface of the forceps jaws and the central lumen of the bushing end cap, to produce low velocity fluid irrigation, or to allow vacuum suction to occur.

In one example, fluid flow is provided via a battery powered fluid pump integrated into the device handle, with a fluid line connecting the pump to the fluid supply consisting of an elevated intravenous saline bag. A separate connector in the handle attaches to a vacuum line that utilizes a standard operating room vacuum source. A specialized spring-loaded three-way control valve is included on the device handle, which may be actuated between two positions, to provide either fluid flow or vacuum to the lumen of the outer sheath. In its normal resting position, the valve permits fluid flow to occur. When the suction control button is pressed, the valve shuttles to its second position, cutting off fluid flow while opening the vacuum line.

In one example, fluid flow is provided by a battery powered electric pump activated by depression of an electrical button switch in the device handle. Two nine-volt batteries supply power to the pump via an electronic control board that maintains a constant voltage delivery to ensure that a constant fluid jet velocity is achieved for reliable tissue hydro dissection. A rotational switch that controls a potentiometer may also be provided on the instrument handle to allow the surgeon to adjust the velocity of the hydro dissection jet.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

FIGS. 6*a*-6*c* illustrate details of a distal portion of the device of FIG. 5.

FIGS. 7*a* and 7*b* depict an exemplary profile of the jaws of the device of FIG. 5 in closed and open configurations, respectively.

FIG. 12 is a table showing results of exemplary water jet flow rate testing.

FIGS. 17*a*-17*e* illustrate activation of a low velocity fluid irrigation and a high velocity fluid jet with the hydro dissection, irrigation, and suction laparoscopic forceps.

DETAILED DESCRIPTION

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Figure 1A:
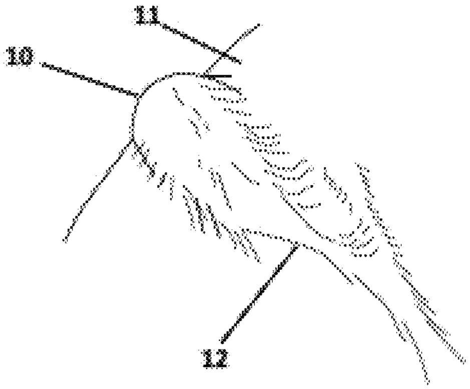
FIGS. 1*a* and 1*b* depict the appearance of an exemplary non-gangrenous and gangrenous gallbladder, respectively.
Figure 1B:
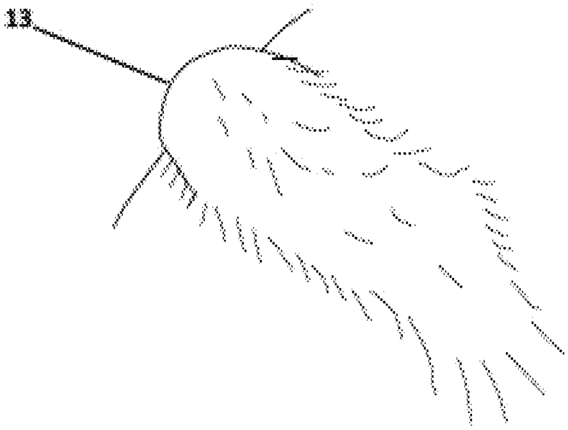

Turning to the drawings, FIG. 1*a* illustrates an example of the surgical appearance of a gallbladder 10 attached to the underside of a liver 11, in a non-gangrenous situation. The outline of the cystic duct 12 may typically be observed in a non-gangrenous laparoscopic cholecystectomy surgery. FIG. 1*b* depicts an example of a gangrenous gallbladder 13, that is enlarged, swollen and edematous. The outline of the gangrenous gallbladder 13 and normal surrounding anatomical landmarks are obscured by the inflamed and edematous tissue.

Figure 2A:
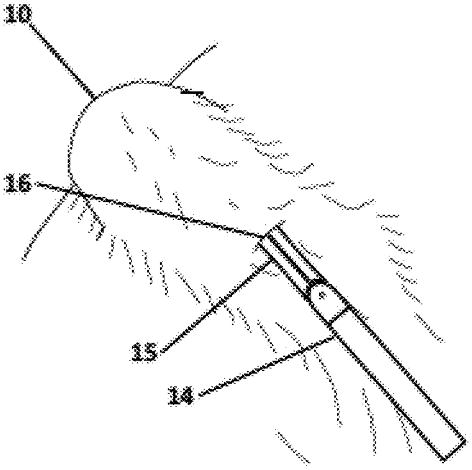
FIGS. 2*a* and 2*b* show exemplary maneuvers used in mechanical blunt dissection of tissue.
Figure 2B:
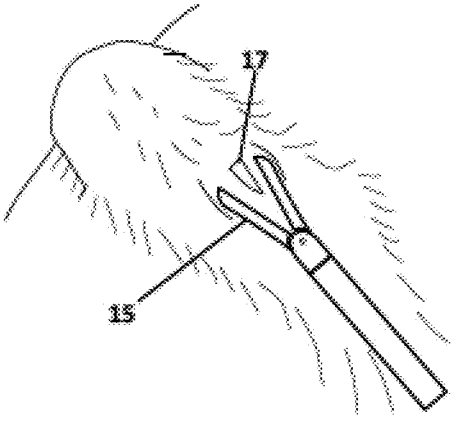

FIG. 2*a* depicts an example of mechanical blunt dissection of the gallbladder 10 using conventional laparoscopic forceps 14. The tips of the jaws 15 of the laparoscopic forceps 14 are inserted into tissue at an entry site 16, with the jaws 15 in a closed orientation. Following tissue insertion, the jaws 15 are forcibly opened, as shown in FIG. 2*b*, to dissect the tissue of gallbladder 10, creating a cleavage plane or opening 17 in the bluntly dissected tissue. Blunt mechanical dissection of tissue is generally safe to perform when the gallbladder is non-gangrenous, and underlying anatomical structures such as blood vessels and ducts are visually perceived. If underlying blood vessels and ducts are obscured, however, e.g., due to tissue edema and inflammation in the event of gangrenous cholecystitis and the like, laceration, perforation, and/or transection of blood vessels and ducts may occur upon blunt dissection maneuvers using conventional laparoscopic forceps. Application of a fluid jet to dissect tissue in gangrenous gallbladder may be useful, as a moderately pressurized fluid jet imparts less force than rigid forceps jaws during tissue dissection, particularly in inflamed and edematous tissue that is more friable than normal tissue.

Figure 3A:
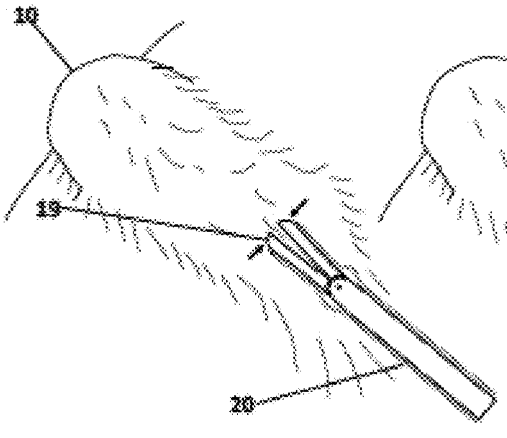
FIGS. 3*a*-3*c* depict an exemplary sequence of steps that may be used in hydro dissection of tissue, e.g., using the hydro-dissection devices described herein.
Figure 3B:
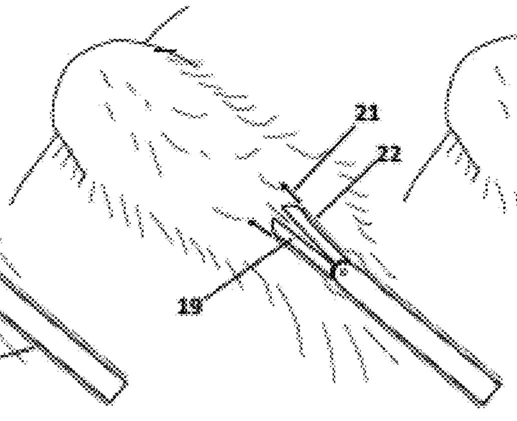
Figure 3C:
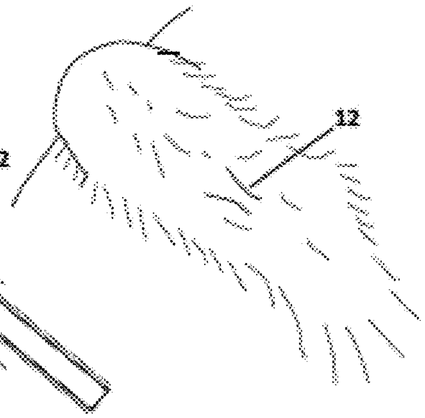

FIG. 3*a*-3*c* illustrate an exemplary technique of atraumatic tissue dissection using a hydro dissection laparoscopic forceps device 20. In FIG. 3*a*, the jaws 19 of the hydro dissection forceps 20 gently close on tissue of the gallbladder 10 without its tips puncturing into the tissue. Following closure of the jaws 19, the hydro dissection forceps device 20 may remain in a fixed position, i.e., the device 20 is not moved to tear or otherwise displace tissue. In FIG. 3*b*, following fixation of the tissue by closure of the jaws 19, fluid jets 21 are initiated, e.g., lateral to each jaw 19. The closed jaws 19 fixate tissue and provide counter traction as the fluid jets 21 exert hydro dissection force against tissue lateral to the region grasped by the jaws 19. Tissue separation is performed solely by hydro dissection, and avoidance of conventional blunt dissection maneuvers involving tissue tearing and tissue puncture leads to atraumatic isolation of anatomic structures, such as the duct 12 observed in FIG. 3*c*.

Figure 4:
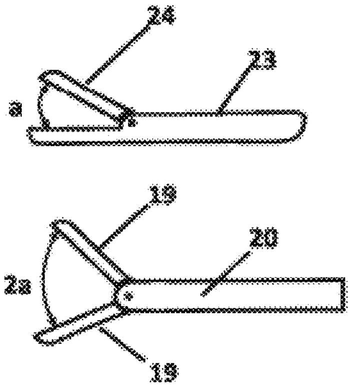
FIG. 4 illustrates exemplary differences in width of jaw opening between a single action jaw instrument and a double action jaw instrument.

FIG. 4 illustrates functional differences that may be experienced between forceps 23 with a single action jaw 24 and double action forceps 20 with two moveable jaws 19. Jaws 19 of double action forceps 20 open twice as wide as forceps 23 with a single moveable jaw 24, permitting a surgeon to grasp a larger amount of tissue between the jaws 19 for enhanced tissue control and avoidance of tissue slippage out of the grasp of jaws 19. Proper tissue fixation is necessary to provide requisite counter traction during lateral hydro dissection procedures, particularly with the wet tissue environment encountered with the technique. Thus, double action, movable jaws 19 may provide advantages over a single action jaw 24 during tissue dissection.

Figure 5:
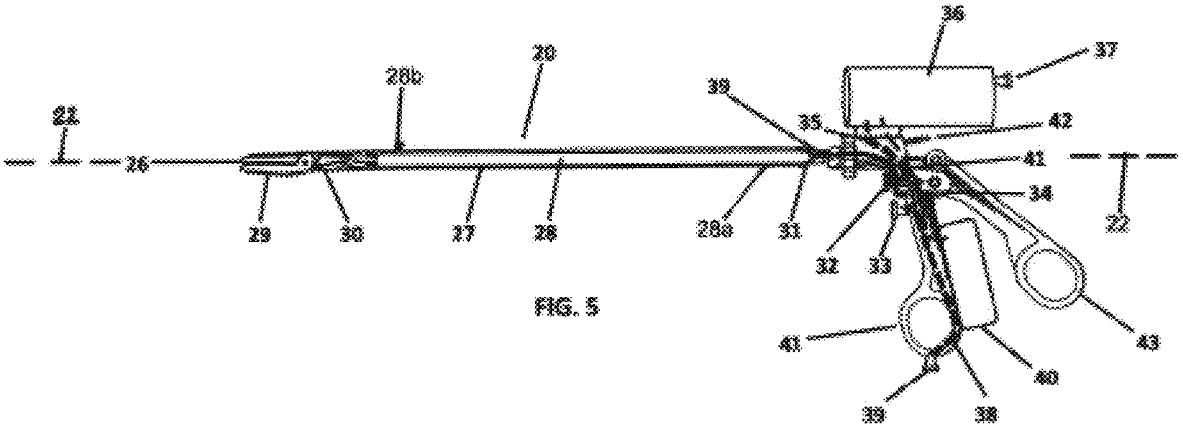
FIG. 5 depicts exemplary components of a hydro dissection laparoscopic forceps device.

Turning to FIG. 5, exemplary components are shown that may be included in a hydro-dissection laparoscopic graspers device 20. Generally, the device 20 includes an elongate shaft 28 defining a longitudinal axis 22, e.g., a substantially rigid tubular or solid shaft, including a proximal end 28*a* and a distal end 28*b* sized for introduction into a patient's body. The shaft 28 may include a pair of shaft channels 27, e.g., including diametrically opposed rigid fluid supply tubes 27 attached to lateral aspects of the shaft 28. Alternatively, the shaft channels 27 may be integrally formed in the wall of the shaft 28, e.g., by one or more of extrusion, molding, casting, machining, and the like. In a further alternative, the shaft 28 may include a single channel or infusion lumen extending from the proximal end 28*a* to the distal end 28*b* and a fitting split, or other branch (not shown) may be provided on the distal end to provide two openings that may be connected to respective flexible tubes and jaw channels 29.

The device 20 includes a pair of jaws 26 on the distal end 28*b* of the shaft 28, e.g., that may be manipulated between a closed position (e.g., as shown in FIG. 7*a*) and an open position (e.g., as shown in FIG. 7*b*), via manipulation of an actuator 43 on a handle 41 on the proximal end 28*a* of the shaft 28. In the example shown, the handle 41 includes a stationary ring extension 41 and a moveable ring actuator 43 coupled to the jaws 26 to direct them between the closed and open positions. As best seen in FIG. 6*a*, the jaws 26 are coupled to the distal end 28*b* of the shaft 28 such that, manipulation of the actuator 43 causes both jaws 26 to move laterally away from the axis 22 when the jaws 26 are opened and the jaws 26 are generally aligned along the axis 22 when the jaws are closed, e.g., as shown in FIGS. 5 and 7*a*. Alternatively, the device may include only a single movable jaw and a fixed jaw attached to or otherwise extending from the distal end of the shaft (not shown), e.g., similar to the forceps 23 shown in FIG. 4. In this alternative, an actuator may move the single jaw between open and closed positions to grasp tissue between the jaws.

Optionally, the jaws 26 may include substantially blunt surfaces to prevent puncturing, cutting, and/or otherwise damaging tissue. For example, as shown, the inner contact surfaces 26*a* and/or the distal tips 26*b* of the jaws 26 may include flat and/or rounded edges to allow tissue to be grasped between the jaws 26 with minimal risk of tearing or cutting. Alternatively, a different end effector may be provided than the blunt jaws 26. For example, the jaws may include sharpened inner edges and/or pointed tips, e.g., to provide a scissors or other cutting instrument (not shown). In another alternative, a stapler or clip applier may be provided for the end effector, e.g., including one or more staples or clips carried by one of the jaws and an anvil or other structure on the opposite jaw (not shown) to allow one or more staplers or clips to be applied through tissue contacted between the jaws.

As best seen in FIG. 6*a*, fluid supply tubes 29 may be attached and/or otherwise provided on the jaws 26, e.g., extending along lateral aspects of the jaws 26 on opposite outer longitudinal edges. For example, separate substantially rigid tubular segments may be formed and permanently attached to the outer edges of the jaws 26, e.g., by one or more of bonding with adhesive, welding, soldering, brazing, fusing, and the like, or, alternatively, the jaw tubes 29 may be integrally formed with the jaws 26. A flexible tube 30 extends from each shaft channel 27 to a respective jaw tube 29, e.g., attaching the distal end of shaft fluid supply tubes 27 to jaw fluid supply tubes 29 in a fluid tight manner. The flexible tubes 30 allow fluid delivery while the jaws 26 are opened, closed, or partially open.

In one example, when the jaws 26 are closed, the outer profile of the working portion of the device 20, including the jaws 26, fluid supply channels 29 and 27, and flexible tubes 30 do not exceed about five millimeters (5 mm) or other maximum outer diameter or cross-section, e.g., to allow the device 20 to be introduced into the body through a corresponding sized access device, e.g., a five millimeter (5 mm) laparoscopic or thoracoscopic trocar, delivery sheath, and the like (not shown).

Optionally, the graspers 20 may be connected to a radiofrequency power source (not shown), e.g., via a connector 42 on the proximal end 28*a*, e.g., on handle 41 as shown in FIG. 5, to allow the jaws 26 to cauterize blood vessels, ducts, and/or other tissue, similar to conventional laparoscopic graspers. The connector 42 may be coupled to the jaws 26 by one or wires or other leads (not shown) extending between the proximal and distal ends 28*a*, 28*b* of the shaft 28, which may, in turn, to electrically conductive electrodes or surfaces on the jaws 26. For example, the entire inner contact surface 26*a* of the jaws may be coupled to the leads to deliver electrical energy to tissue contacted between the jaws 26, if desired. Optionally, the jaws 26 may include one or more sensors, e.g., a Doppler sensor (not shown) on one of the jaws that may be used to identify blood flow in tissue captured between the jaws or otherwise contacted by the sensor(s). A processor (not shown) may be coupled to the sensor(s) and/or cautery elements to provide an output to the user when blood is flowing and/or discontinued, e.g., for use in conjunction with cauterizing contacted tissue.

Pressurized fluid for hydro-dissection is supplied by a miniature fluid pump 36 included in or coupled to the handle 41, e.g., integrated into the superior aspect of the stationary portion of the handle 41. The fluid pump 36 may include a connector, e.g., a female luer fitting 37, that accepts an intravenous fluid line connected to a saline bag or other source of fluid (not shown), e.g., containing one to three (1-3) liters or other desired volume of sterile saline. In one example, a fluid supply line 35 extends from the pump 36 to a normally closed fluid irrigation trumpet valve 32 provided on the handle 41.

Optionally, a connector 39 may be provided to connect a source of vacuum or suction (not shown) to the device 20, e.g., communicating with the shaft channels 27. For example, as shown in FIG. 5, the stationary handle portion 41 may include a suction luer fitting 39 that allows the hydro-dissection laparoscopic graspers 20 to be connected to wall suction in the operating or procedure room, for evacuation of fluid via jaw channels 29. As shown, a suction connecting tube 38 extends from luer fitting 39 to the inlet of a suction trumpet valve 33, which is also in a normally closed position until the trumpet valve 33 is depressed.

In one example, the outlets of both irrigation trumpet valve 32 and suction trumpet valve 33 are connected together to a common fitting 34 with a connecting line 39 extending to a connector 31 that is attached to both fluid supply tubes 27. Thus, in this example, depression of the irrigation trumpet valve 32 causes fluid dissection jets to emanate from both fluid supply tubes 27, while depression of the suction trumpet valve 33 causes suction of fluid via the shaft and jaw channels 27, 29. If the jaw and/or shaft channels 29, 27 become clogged during actuation in the suction mode, the irrigation mode may be activated to clear debris lodged in channels 29, 27.

FIG. 6*a* depicts an enlarged view of the jaws 26 and the distal end 28*b* of the shaft 28 of the device 20. Each jaw channel 29 is attached to or otherwise extends from the lateral aspect of jaw 26, e.g., along the outer edge of each jaw 29. A proximal end of each jaw channel 29 may be offset distally from the hinge connecting the jaws 29, e.g. offset about three millimeters (3 mm) from the proximal end of each jaw 26, e.g., to provide circumferential clearance to permit attachment of the flexible tube 30 and/or accommodate rotational movement of the jaws 26. Similarly, each shaft channel 27 is attached to or otherwise extends axially along either side of the shaft 28, except for desired offset, e.g., about a three millimeters (3 mm) long length of its distal portion, where circumferential clearance permits attachment of the proximal end of flexible tube 30.

An actuator may be coupled to the jaws 26 to manipulate the jaws between the open and closed positions. For example, as shown, the jaws 26 are opened and closed via advancement and retraction using an elongate member, e.g., a stainless steel rod 44 that extends through the length of shaft 28 and connects to jaw actuation linkage 45. FIG. 6*b* is a cross-section of the shaft 28, showing a central channel 46 that accommodates actuation rod 44 in a sliding fashion within its lumen. In the example shown, two lateral grooves 47 may extend the length of shaft 28, to allow the attachment of fluid tubes 27, which may be elliptical rather than circular in cross-section, if desired, to increase its luminal area for maximal fluid delivery. Optionally, a relatively thin outer sheath 48, e.g., composed of polymer heat shrink or other material, may cover the shaft 28 and attached fluid tubes 27, to provide a substantially smooth outer surface for insertion and sealing in a laparoscopic trocar port, and/or to electrically insulate the outside of shaft 28 as radiofrequency current is applied to cauterize tissue grasped by jaws 26.

FIG. 6*c* is an end view of an exemplary instrument jaw 26, illustrating the attachment of a fluid tube 29 to its lateral aspect. If desired, the jaw 26 may be thinned out, or a groove may be cut along its length to allow attachment of fluid tube 29 while maintaining a desired outer profile, e.g., not more than about five millimeters (5 mm) when jaws 26 are closed. The fluid tube 29 may be attached to the lateral aspect of jaw 26 using one or more of adhesive, solder, braze, weld, and the like. The attachment material may form a contoured fillet 49 along the length of the attached tube 29, to yield a smooth profile of the lateral aspect of the jaw 26, for atraumatic tissue contact during surgery.

FIG. 7*a* depicts the hydro-dissection laparoscopic forceps 20 with the jaws 26 in a closed position. In the example shown, the flexible fluid supply connecting tubes 30 remain substantially flush against the forceps 20 when jaws 26 are closed, allowing unimpeded insertion through a desired access device, e.g., a 5 mm endoscopic trocar (not shown). FIG. 7*b* shows forceps 20 with the jaws 26 in an open position. Flexible connecting tubes 30 splay out laterally when the jaws 26 are opened. Forceps 20 insertion and removal must be conducted only with closed instrument jaws 26.

Figures 8A, 8B, 8C:
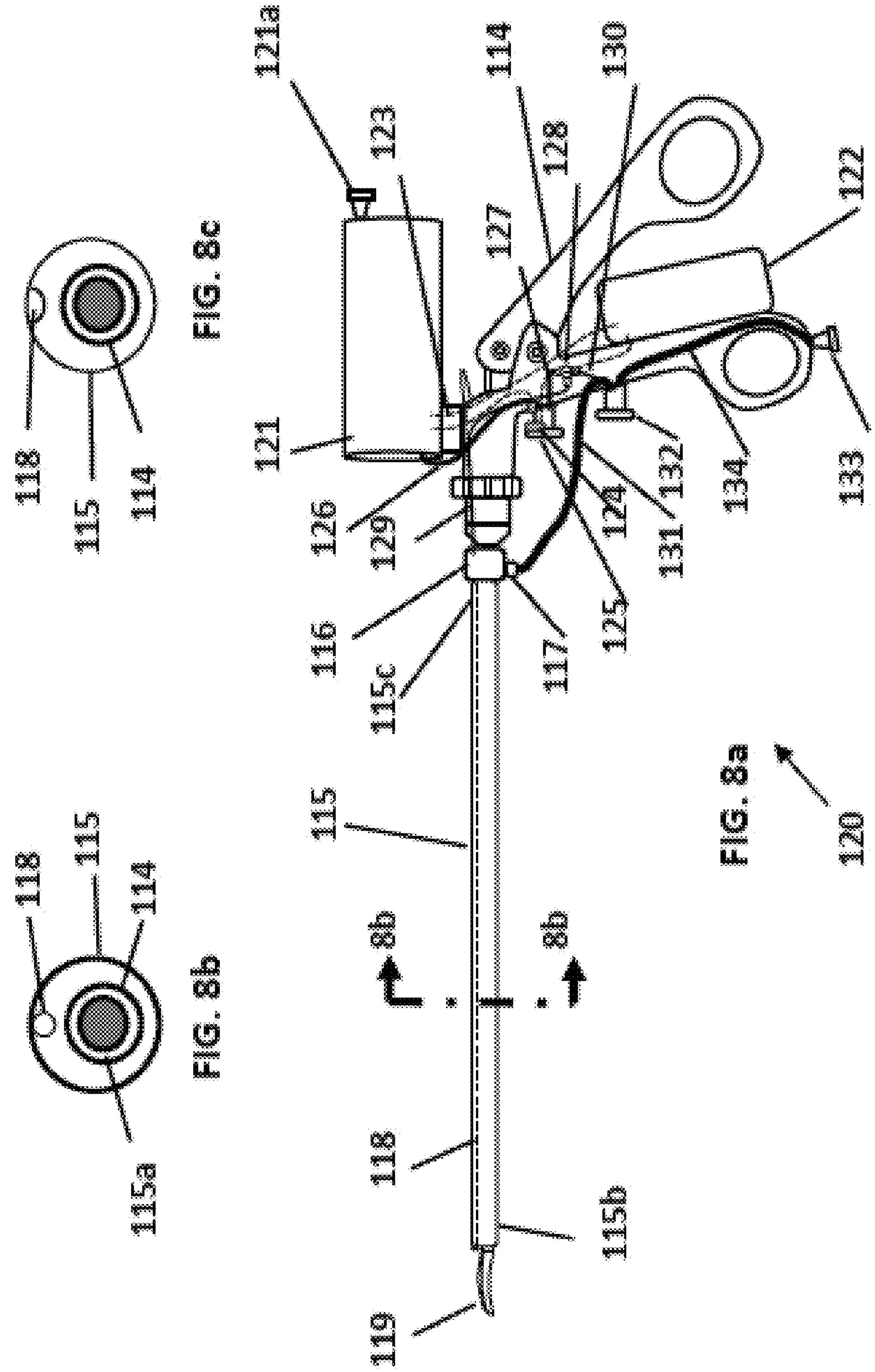
FIG. 8*a* shows another example of an apparatus that may provide hydro-dissection, irrigation and suction in a unitary format including a forceps movable relative to an outer sheath.
FIG. 8*b* is a cross-sectional view of the device of FIG. 8*a* taken along section 8*b*-8*b*.
FIG. 8*c* is a cross-sectional view of an alternative configuration of the device of FIG. 8*a*.

Turning to FIG. 8*a*, another example of an apparatus 120 is shown that includes an outer sheath 115 and a forceps instrument 114 that may be used to selectively provide hydro-dissection, irrigation, and/or suction, e.g., as needed during a surgical procedure. In the example shown, the forceps 114 and outer sheath 115 may be manufactured and provided separately but, before or during a procedure, the forceps 114 may be inserted into the sheath 115 to allow the different modes of operation. For example, the sheath 115 may be made to accommodate inserting a conventional forceps instrument (or alternatively, another instrument, such as a bowel grasper, scissors, clip applier, vessel scaler, and the like not shown) to provide hydro-dissection and/or irrigation/suction during use of the conventional instrument. Alternatively, the forceps 114 may be manufactured integrally with the sheath 115, yet may be movable axially to advance or retract the forceps 114 as desired during a procedure.

Figure 9A:
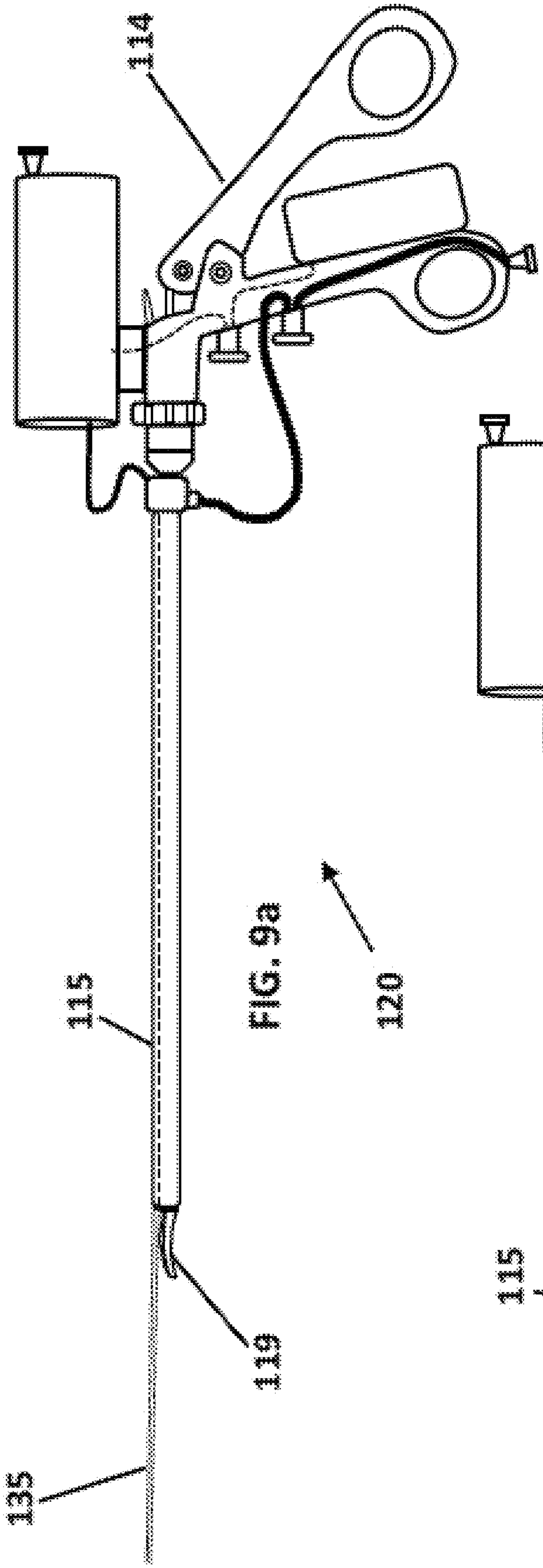
FIG. 9*a* shows the device of FIG. 8*a* with the forceps advanced relative to the sheath to allow mechanical dissection, irrigation, and/or hydro-dissection.
Figure 9B:
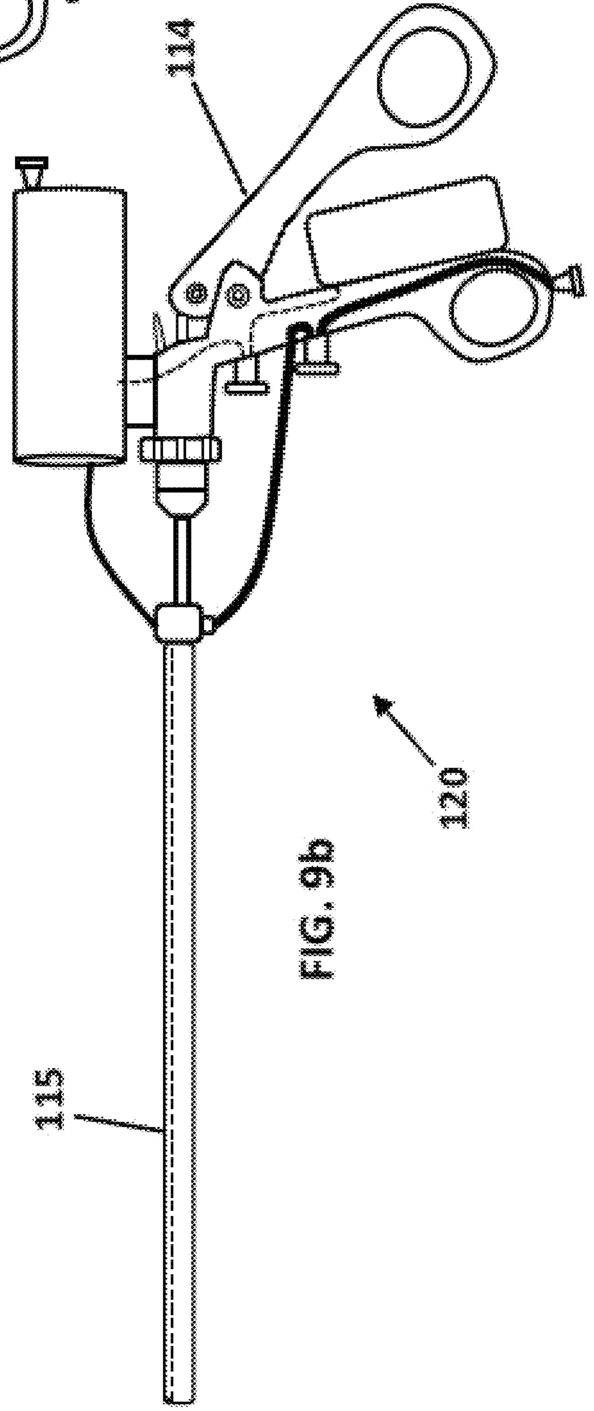
FIG. 9*b* shows the device of FIG. 8*a* with the forceps retracted into the sheath to allow hydro-dissection, irrigation, and/or suction.

For example, as shown, a conventional three millimeter (3 mm) or smaller laparoscopic forceps 114 may be provided that is inserted through a primary or central lumen 115*a* of the outer sheath 115 (e.g., shown in FIG. 8*b*), e.g., such that jaws 119 of the forceps 114 extend distal to a distal tip 115*b* of sheath 115, e.g., as shown in FIGS. 8*a* and 9*a*. A fluid tight valve or other seal 116 may be provided on a proximal end 115*c* of sheath 115, e.g., such that the valve 116 slidably seals against the shaft of the forceps 114, and allows axial and/or rotational movement of the forceps 114 and sheath 115 relative to one another. For example, the valve 116 may allow advancement of the sheath 115 to retract the jaws 119 of the forceps 114 into the lumen 115*a* of the sheath 115, e.g., as shown in FIG. 9*b*, as well as rotation, while providing a fluid-tight seal to prevent fluid introduced into the lumen 115*a* from leaking.

The sheath 115 may include one or more ports communicating with the central lumen 115*a*, e.g., to allow fluid and/or suction to be applied. For example, as shown, a side port 117 is provided on the valve 116, which may be coupled to a source of fluid or vacuum to allow injection or removal of fluid in the surgical field via the sheath 115, i.e., through the distal opening of the primary lumen 115*a* at the tip 115*b*.

In addition, the sheath 115 may include one or more additional or secondary lumens or channels extending between the proximal and distal ends 115*c*, 115*b*. For example, as shown, a relatively small, e.g., about 0.0325 inch (0.81 mm) inner diameter, hydro dissection fluid channel 18 may be attached to the sheath 115, e.g., extending along an inner surface of the sheath 115 adjacent the central lumen 115*a*, as shown in FIG. 8*b*. The secondary fluid channel 118 may extend the length of the sheath 115 to provide an outlet at the distal tip 115*b*, which may be used to generate a high velocity jet for tissue dissection, as explained further elsewhere herein. Thus, relatively low velocity fluid irrigation may be supplied via the central lumen 115*a* of the sheath 115, and/or high velocity jet may be supplied via the secondary channel 118, as selected at any given time by a surgeon or other use.

Figure 10:
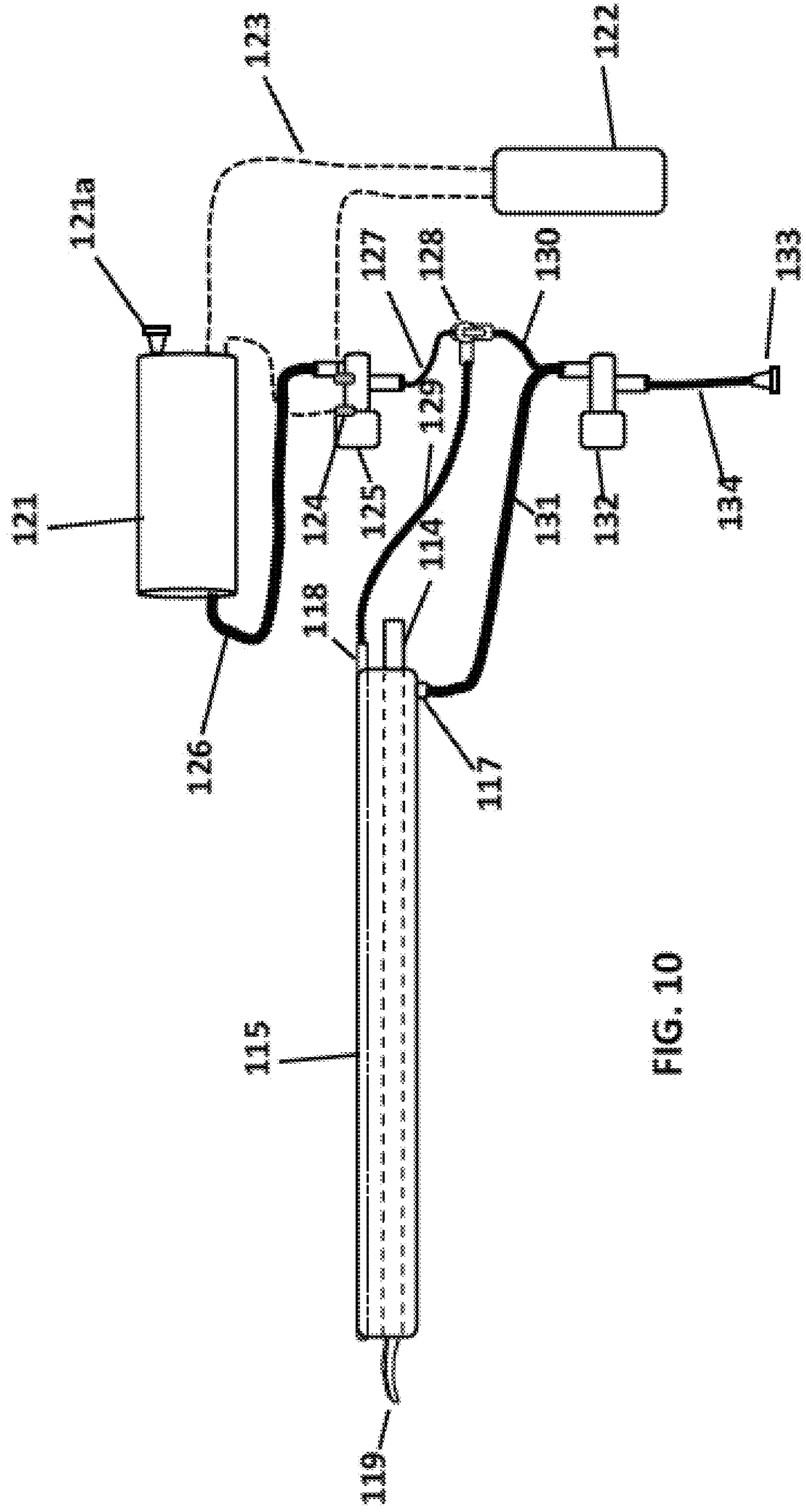
FIG. 10 is a schematic showing exemplary fluid pathways (solid lines) and electrical pathways (dashed) that may be included in the device of FIG. 8*a*.

In the example shown, the fluid flow may be driven by a battery powered diaphragm pump or other fluid source 121 mounted or otherwise provided on the apparatus 120, e.g., rigidly attached to a superior aspect of a handle of the forceps 114. Alternatively, an external pump or other fluid source (not shown) may be provided that may be connected to the apparatus 120. A luer fitting or other connector 121*a* may be provided on the pump 121 that may be connected to a source of fluid, e.g., a line from an intravenous saline bag (not shown). Pressurized fluid may exit the pump 121 via pump supply line 126, which connects to a fluid control valve 125. In one example, the fluid control valve 125 may be a trumpet valve that includes an electrical switch 124, e.g., leading from a nine-volt battery or other power source 122 to the pump 20, e.g., as best seen in FIG. 10. Depression of the fluid control valve 125 opens the valve 125 to fluid flow and may power the pump 120 simultaneously.

In the exemplary schematic shown in FIG. 10, the output from the fluid control valve a25 leads to a three-way stopcock a28 or other control, that allows the user to select either hydro-dissection flow line 129 to the channel 118, or low velocity irrigation via the central lumen 115*a* of the sheath 115. Alternatively, the device may include a processor or controller (not shown) that may automatically open and close the appropriate flow line based on the actuator pressed by the operator to alternatively deliver hydro-dissection or irrigation flow. As shown, a low velocity irrigation line 130 exits the stopcock 128, and taps into an output suction line 117 exiting suction control valve 132. The input line 134 to a suction control valve 132 leads to a vacuum fitting 133, e.g., on the inferior aspect of the handle of the forceps 114. The fitting 133 may be connected to a source of vacuum, e.g., a line from the operating room vacuum source to provide suction capability via the central lumen 115*a* of the sheath 115, e.g., when the suction control valve 132 is depressed. Alternatively, low velocity fluid irrigation may be delivered through the central lumen 115 of the sheath 115, e.g., to unclog the apparatus 120 when tissue debris and blood clots have reduced the suction capability.

FIG. 8*b* is an exemplary cross-sectional view of the sheath 115, illustrating a small diameter tubular body attached to a superior aspect of the central lumen 115*a* of the sheath 115 to provide the secondary channel 118. As shown, the shaft of the forceps 114 occupies a portion of the central lumen 115*a* while providing area around the shaft to accommodate irrigation and/or suction. FIG. 8C is a cross-sectional view of an alternative construction of the sheath 115, in which the sheath 115 is a polymer extrusion or other integral tubular body that includes a secondary lumen 118 integrally formed within the wall of the sheath 115 adjacent the primary lumen 115*a*.

FIG. 10 shows an exemplary schematic depicting the fluid and electrical systems of the apparatus 120. In the example shown, the fluid diaphragm pump 121 receives fluid input via luer fitting 121*a*, and fluid exits via the output line 126. The battery 122 supplies power to the pump 121 via conducting electrodes 123, with a power switch 124 integrated into the fluid control trumpet valve 125. The fluid control trumpet valve 125 is normally in an off position, and power switch 124 normally in an open position. When the fluid control trumpet valve 125 is depressed, the valve 125 opens to fluid flow, and the power switch 124 is simultaneously closed to supply current to the pump 20. The fluid output line 127 from the fluid control valve 125 forms the input into the three-way stopcock 128, which allows the surgeon to select one of two outputs—either hydro dissection output line 129 connecting to the small diameter fluid supply channel 118, or the low velocity irrigation output line 130. The irrigation output line 130 connects to suction supply line 131, which leads from the output of suction control valve 132 to the side port 117 in communication with the central lumen 115*a* of the sheath 115. Suction is provided by connection of the operating room vacuum source to suction connector 133, with the suction line 134 forming the input to the suction control valve 132. When low velocity irrigation is selected via depression of fluid control valve 125 with the three-way stopcock 128 set to the irrigation output line 130, the suction control valve 132 is closed, and fluid flows through the suction supply line 131 into the central lumen 115*a* of the sheath 115.

FIG. 9*a* depicts the apparatus 120 in the configuration with the sheath 115 retracted (or the forceps 114 advanced) to expose the jaws 119 of the forceps. In this configuration, the jaws 119 may be used to perform one or both of the following techniques: (1) surgical tissue manipulation and mechanical blunt dissection; and (2) hydro dissection with tissue counter-traction, i.e., by first grasping tissue between the jaws 119 before activating the jet. As described elsewhere herein, hydro dissection with tissue counter-traction may be performed by holding tissue stationary with the forceps jaws 119 while high velocity fluid jet 135 emanates from the distal tip 115*b* of the sheath 115 to gently dissect tissue, avoiding tissue, blood vessel and duct disruption associated with mechanical blunt dissection. FIG. 9*b* depicts the apparatus 120 after retraction of the forceps 114 such that the jaws 119 are withdrawn completely into the sheath 115. This configuration may be used to perform one or more of the following techniques: (1) pure hydro dissection without tissue counter-traction; (2) suction via the central lumen 115*a* of the sheath 115, e.g., to remove fluid and debris from the surgical field; and (3) low velocity fluid irrigation, e.g., to remove blood from the surgical field and/or to clear the sheath 115 of blood clots or tissue debris that clog its central lumen.

Figures 11A, 11B, 11C:
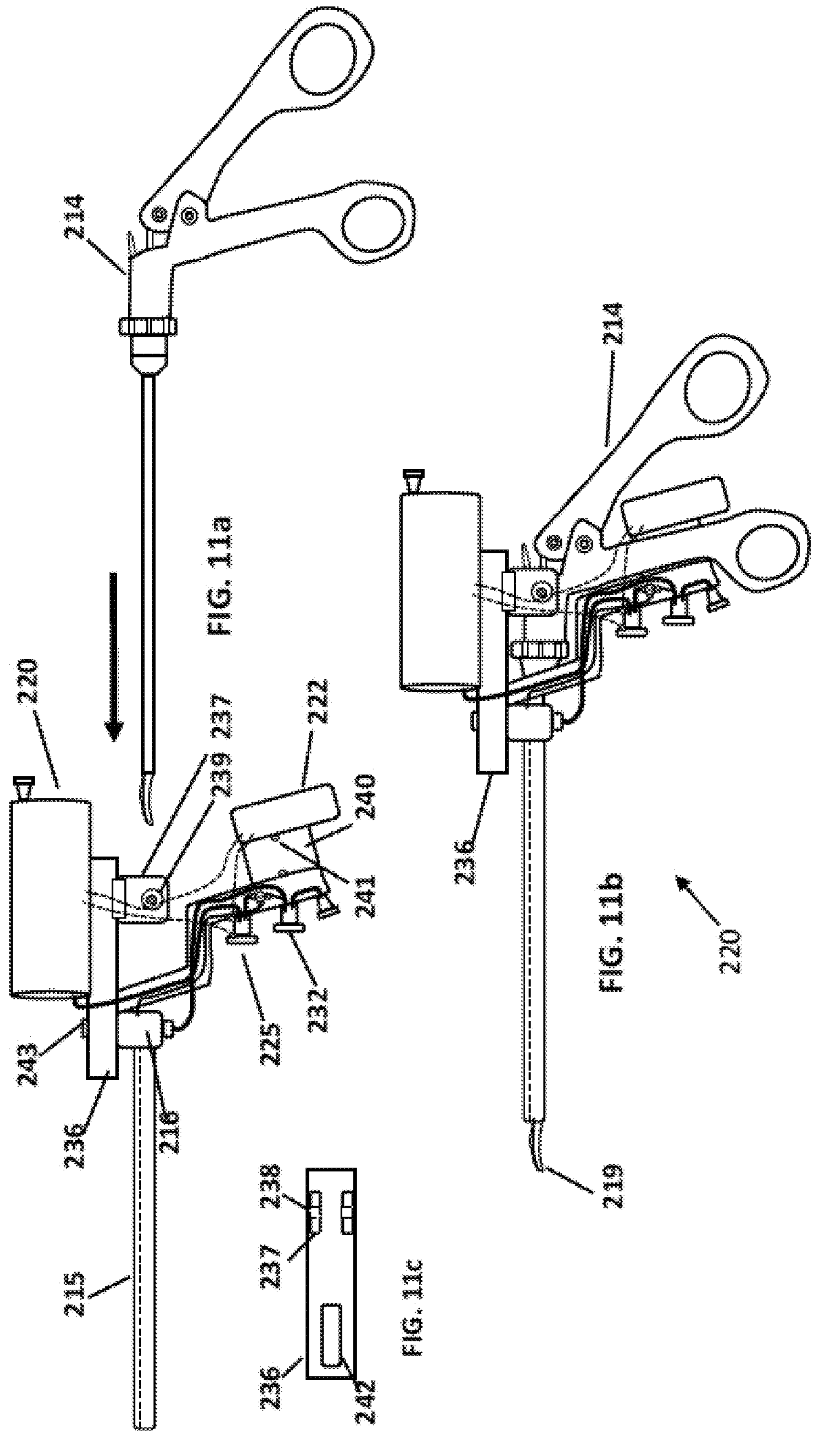
FIG. 11*a* shows another example of an apparatus including a framework including an outer sheath for receiving a separate forceps instrument.
FIG. 11*b* shows the apparatus of FIG. 11*a* with the forceps advanced such that jaws extend from a distal end of the sheath.
FIG. 11*c* is a bottom view of the apparatus of FIGS. 11*a* and 11*b*.

Turning to FIGS. 11*a* and 11*b*, another example of an apparatus 220 is shown that may selectively provide hydro dissection, irrigation and/or suction using a laparoscopic forceps formed of two discrete devices—a frame 236 including an outer sheath 215, fluid pump 220, battery or power source 222, and control valves 225, 232 mounted on the frame 236; and a laparoscopic forceps 214 (or other instrument), generally similar to the previous examples. The laparoscopic forceps 214 may be inserted into the sheath 215, and secured rigidly to the frame 236, e.g., into a channel 237 in the frame 236 using one or more connectors, e.g., setscrews 239 that secure the frame 236 to the handle of the forceps 214. In addition or alternatively, the stationary handle portion of the forceps 214 may be secured to the frame, e.g., snapped into a grooved section 240 of the frame 236 that includes one or more detents 241 in its walls, e.g., to further secure laparoscopic forceps 214.

The sheath 215 may be movable axially relative to the frame 236, e.g., to extend and retract with respect to frame 236 using a pin or other actuator 243, e.g., attached to the valve body 216 of the sheath 215, that translates within a slot 242 in the frame 236, as shown in FIG. 11*c*. Alternatively, the forceps 214 may be movable axially relative to the sheath 215 between distal and proximal positions. FIG. 11*b* shows the assembled configuration of the forceps 214 in the hydro dissection frame 236, with the forceps jaws 219 in the distal position, i.e., extended distal to the tip of the sheath 215. FIG. 11*c* shows the underside of the frame 236, with the sides of the channel 237 containing threaded holes 238 that accept setscrews for attachment to the handle of the forceps 214. The slot 242 that forms part of the translation mechanism for sheath 215 is also visible.

Thus, during use, tissue may be grasped by the jaws 219, and a hydro-dissection fluid jet may be generated to dissect tissue. If desired, the jaws 219 may be retracted into the sheath 215 and a hydro-dissection fluid jet may be delivered without traction and/or irrigation/suction may be generated. Optionally, the forceps 214 may be rotatable relative to the sheath 215, e.g., to adjust the orientation of the jaws 218 when extended to facilitate grasping tissue. Optionally, the forceps 214 may be removable entirely from the sheath 215 while the distal end 215*b* of the sheath 215 is positioned within a surgical space, e.g., to allow one or more different instruments to be introduced through the sheath 215 to perform additional steps of the surgical procedure.

Figure 13A:
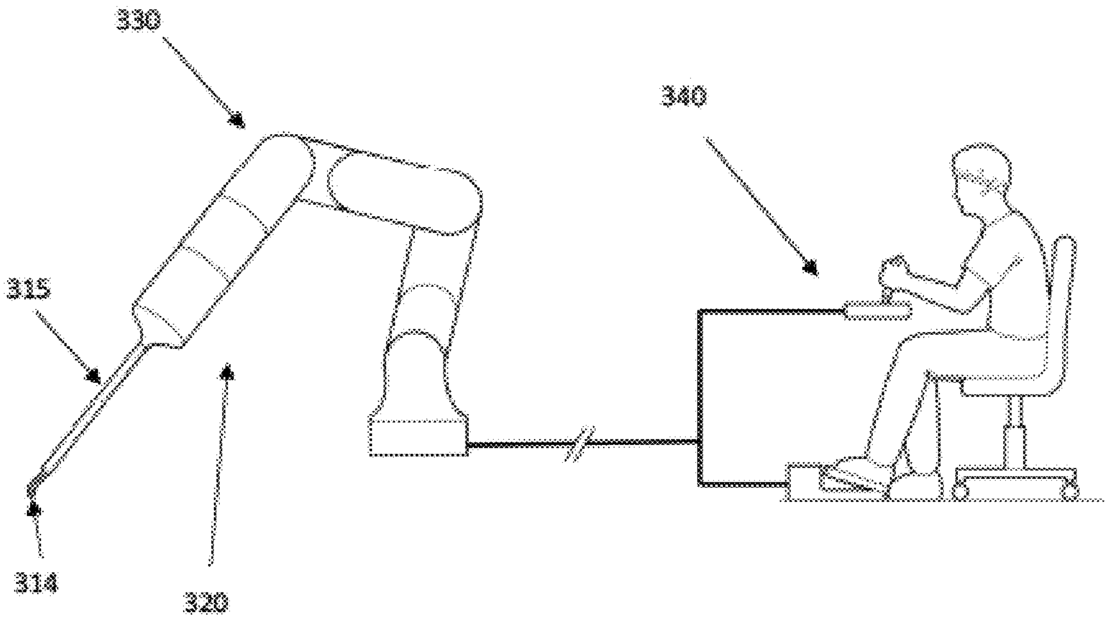
FIG. 13*a* shows another example of an apparatus that provide hydro-dissection, irrigation and suction in a unitary format including a forceps movable relative to an outer sheath connected to a robotic control system.
Figure 13B:
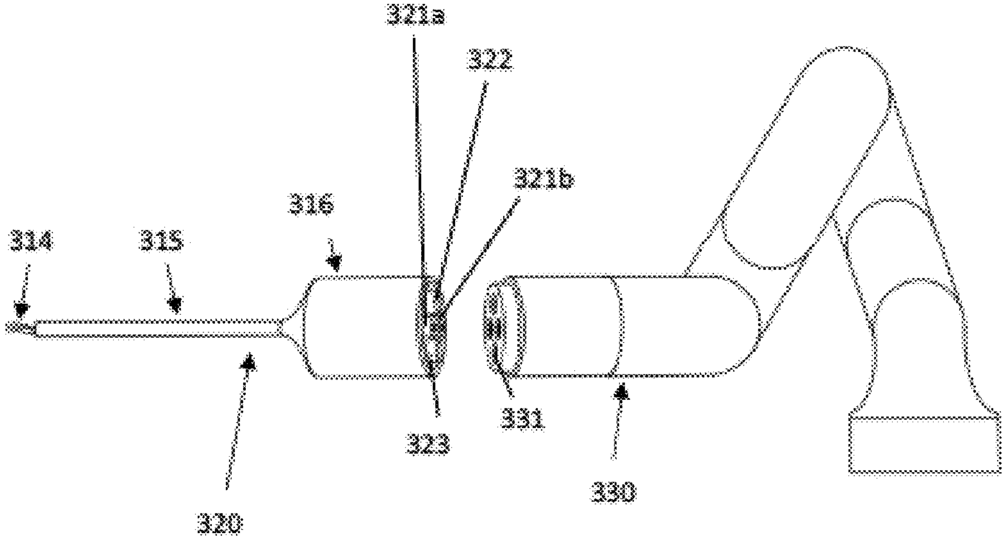
FIG. 13*b* shows an exemplary forceps apparatus connectable to a robotic arm of a robotic surgical system.
Figure 14A:
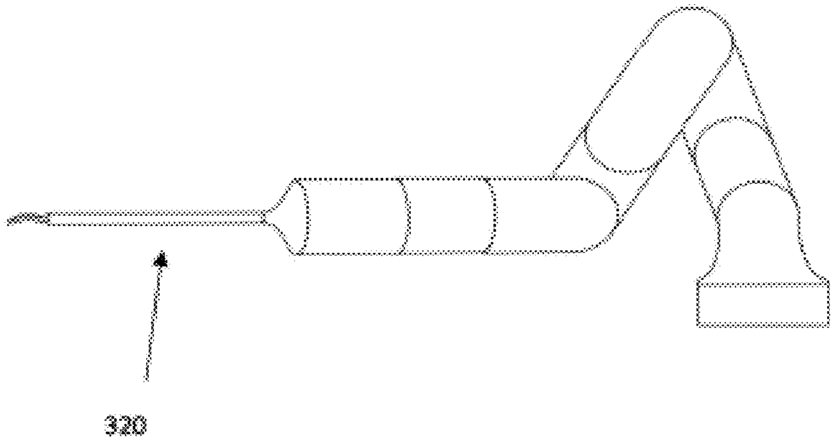
FIGS. 14*a*-14*f* show the apparatus of FIG. 13 with the forceps deployed from (FIGS. 14*a*-14*c*) and retracted into (FIGS. 14*d*-14*f*) the sheath and selectively used to deliver a hydro-dissection jet or irrigation.
Figure 14B:
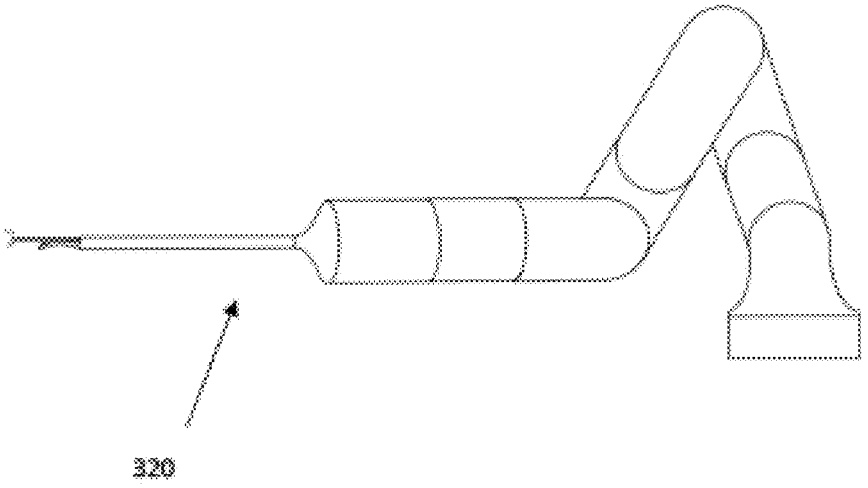
Figure 14C:
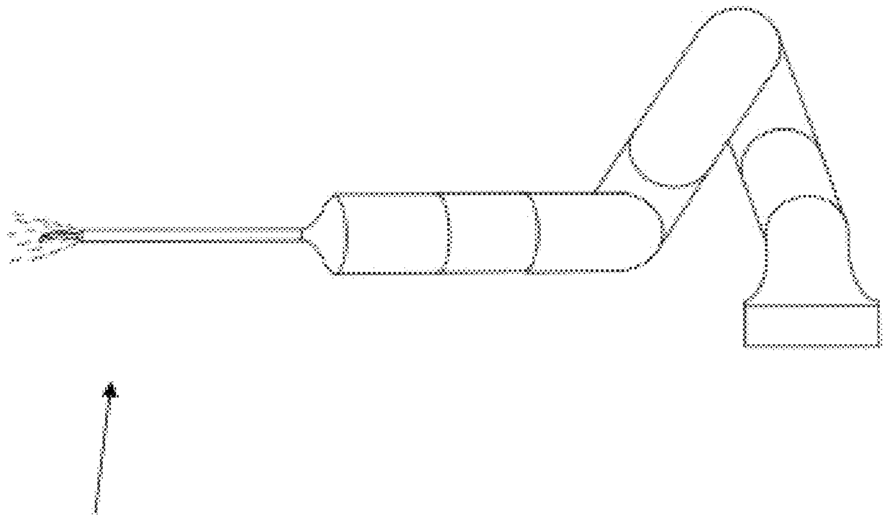
Figure 14D:
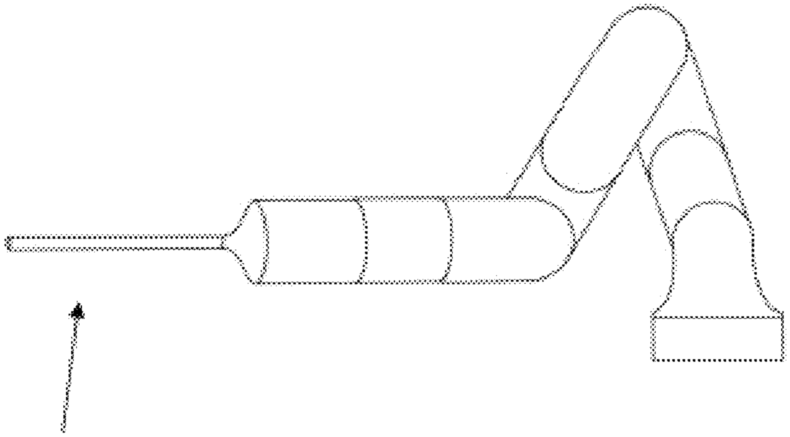
Figure 14E:
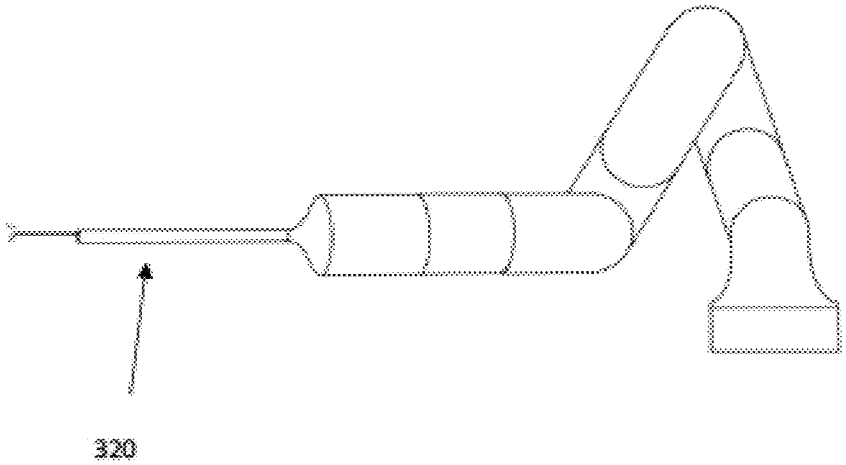
Figure 14F:
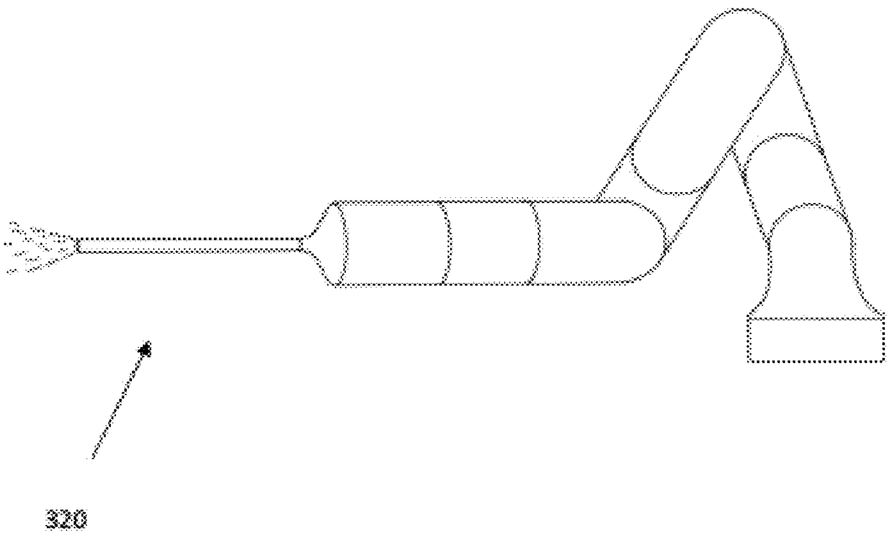

Turning to FIGS. 13-15, another example of a surgical apparatus 320 is shown that includes an outer sheath 315 and a forceps or other instrument 314 including an end effector, e.g., jaws 319, deployable from the sheath 315. Unlike the previous apparatus, the sheath 315 and forceps 314 are mounted to a robotic control arm or system 330, which is coupled to an operator console or system 340, which may be operated remotely by a surgeon. For example, as best seen in FIG. 13B, the sheath 315 may include a proximal mount or housing 316 on its proximal end that may include one or more connectors (not shown) for mounting to an end of the robotic arm system 330. For example, the housing 316 and robotic arm may include one or more mating threads, detents, latches, and the like (not shown) that fix the sheath 315 relative to the robotic arm system 330 such that, once attached, the sheath 315 is manipulated by actuating the robotic arm system 330. As shown, the housing 316 may include one or more ports, knobs, nipples, or other connectors 321-323, for connecting elements of the apparatus 320 to corresponding elements 331 on the robotic arm system 330, as described further elsewhere herein.

As best seen in FIGS. 15A-15F, the sheath 315 includes a primary lumen 315*a* sized to slidably receive a shaft of the forceps 314 and a secondary lumen or jet channel 318 adjacent the primary lumen 315*a*, generally similar to the previous apparatus. The forceps 314 may be movable axially and/or rotatable relative to the sheath 314, e.g., to advance the jaws 319 of the forceps 314 from the distal end 315*b* of the sheath 315, e.g., as shown in FIGS. 14*a*-14*c* and 15*a*-15*c*, or retract the jaws 319 into the sheath 315, e.g., as shown in FIGS. 14*d*-14*f* and 15*d*-15*f*. In addition, similar to the previous apparatus, fluid may be delivered through either of the primary lumen 315*a*, e.g., a low-pressure fluid flow I/S for irrigation, e.g., as shown in FIGS. 14*c*, 14*f*, 15*c*, 15*f*, or the jet channel 318, e.g., a high-pressure fluid jet K for hydro-dissection, e.g., as shown in FIGS. 14*b*, 14*c*, 15*b*, 15*c*.

For example, as shown in FIG. 13*b*, the housing 316 may include a pair of ports 321*a*, 321*b* that communicate with the primary and secondary lumens 315*a*, 318, respectively, that may be coupled to respective ports on the robotic arm system 330 when the housing 316 is connected to the robotic arm 330. These ports, e.g., including one or more seals and/or connectors (not shown) may then communicate with a source of fluid and/or vacuum, e.g., connected to a proximal end of the robotic arm 330. In addition, as shown, the housing 316 includes a first shaft connector 322 that is coupled to a shaft of the forceps 314, which is connected to a corresponding shaft in the robotic arm system 330. Thus, once connected, the robotic arm shaft may be advanced axially and/or rotated about a longitudinal axis, thereby causing corresponding axial and/or rotational movement of the jaws 319 of the forceps 314.

Optionally, if one or more electrodes or other cautery elements are provided on the jaws 319 (or elsewhere on the distal end of the forceps), the housing 316 may include a connector 323, e.g., an electrical connector, that may be connected to a corresponding connector on the robotic arm system 330 to allow activation of the cautery element(s) during use of the apparatus 320. For example, the robotic arm 330 may be coupled to a generator and/or controller (not shown) for providing electrical or other energy to the cautery element(s). Further optionally, if the sheath 315 and/or forceps 314 include other actuatable features, additional connectors may be provided on the housing 316 and robotic arm system 330. For example, if the forceps 314 includes microfluidic channels and/or sensors, connectors may be provided to allow the sensors to be activated during use.

Figure 15A:
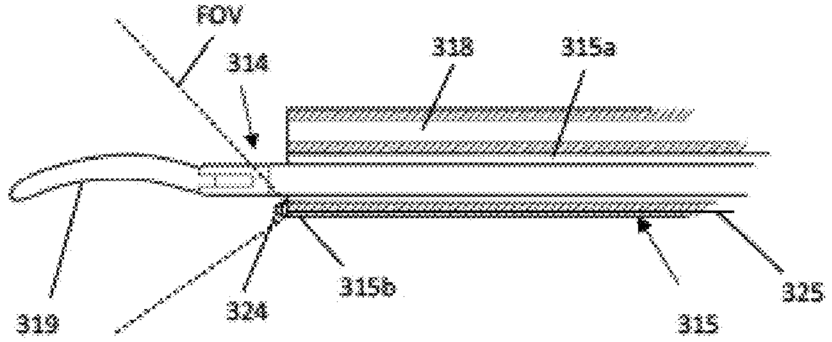
FIGS. 15*a*-15*f* are cross-sectional details of a distal end of the apparatus as shown in FIGS. 14*a*-14*f*, respectively.
Figure 15B:
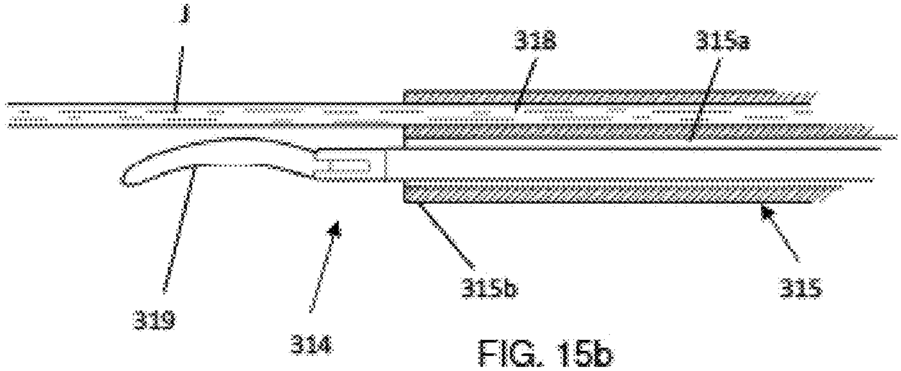
Figure 15C:
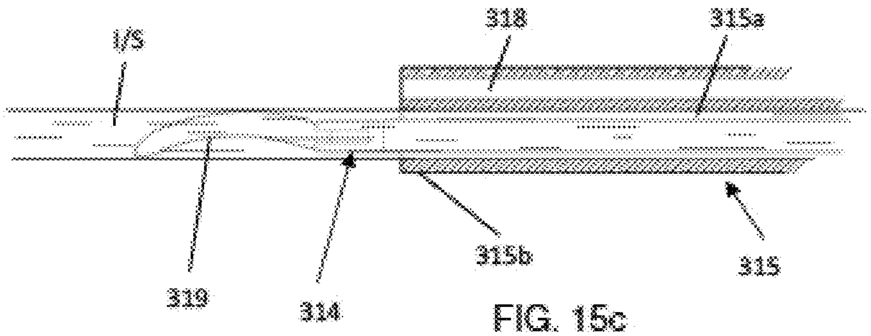
Figure 15D:
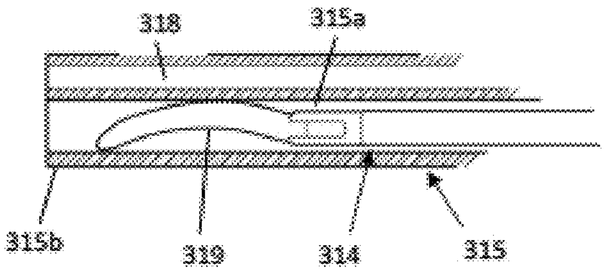
Figure 15E:
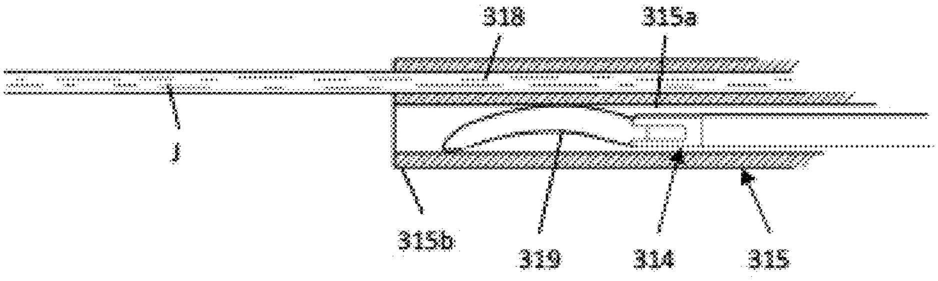
Figure 15F:
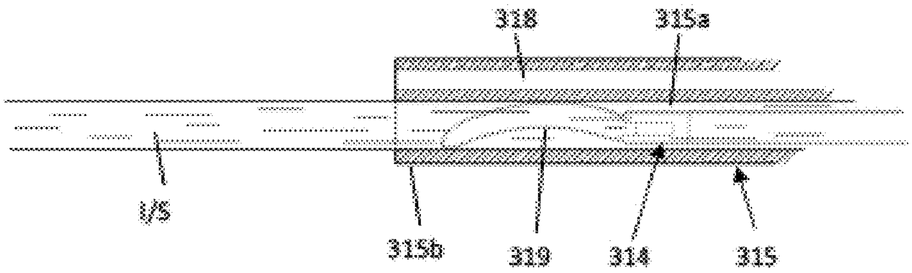

In another option, as shown in FIG. 15A, the sheath 315 may include a camera and/or other imaging element 324 on the distal end 315*b*, e.g., to image the jaws 319 and/or otherwise view beyond the distal end 315*b* of the sheath 315. For example, a CCD, CMOS, or other camera 324 may be provided on the distal end 315*b* having a field of view FOV sufficient to observe the jaws 319 and/or tissue structures within a surgical space into which the device 320 is introduced. In addition, the imaging element 324 may include one or more LEDs or other light sources (not shown), e.g., necessary to illuminate the field of view FOV. One or more leads 325 may be provided, e.g., embedded within the wall of the sheath 315 or provided in a separate lumen (not shown) that extends to the proximal end of the sheath 315. In this option, one or more additional connectors (not shown) may be provided on the housing 316 to provide power to the imaging element(s) and/or to receive signals from the imaging element(s), e.g., to provide signals to a processor of the control console 340 to generate images on a display (not shown) included in the control console 340.

Unlike the previous apparatus, the surgeon may operate the apparatus 320 to manipulate the sheath 315 remotely as desired, e.g., to introduce the sheath 315 into a surgical space, e.g., through a trocar or other access port (not shown), whereupon the forceps 314 may be deployed and manipulated and/or fluid may be delivered into the surgical space to perform hydro-dissection, irrigation, and/or suction, as needed during the procedure. The robotic arm system 330 may be connected to one or more sources of fluid and/or vacuum, e.g., one or more pumps, one or more power sources, one or more processors and/or controllers, and the like (not shown), which may be activated using the control console 340, similar to conventional robotic surgical procedure systems.

Optionally, any of the devices and apparatus described herein may include one or more additional features. For example, if desired, one or more micro-fluidic channels may be provided on the instrument, e.g., extending to the distal end and/or jaws of the forceps, that may include one or more sensors coupled to a processor (not shown) of the apparatus. Signals from the sensor(s) may be analyzed by the processor, e.g., to identify tissues and/or analyze body fluids to identify the presence of one or more diseases or other conditions.

In addition or alternatively, the devices or apparatus may include a Doppler or other sensor, e.g., carried on one or both jaws of the forceps or other end effector, that may be coupled to a processor to identify blood flow in tissues captured between the jaws. Optionally, the devices or apparatus may include one or more electrodes or other cautery elements, vessel sealing elements, and the like, e.g., on one or both jaws or other location on the end effector, which may be coupled to an energy source (not shown), which may be selectively activated to cauterize tissues that are captured or severed by the forceps or other instrument. One or more actuators (also not shown) may be provided on the handle of the forceps or other location of the apparatus or system, which may be used to activate such sensors and/or cautery elements.

Optionally, any of the devices and systems herein may include one or more imaging elements, e.g., on the distal end of the sheath or instrument, e.g., a CCD, CMOS, or other camera and/or one or more LEDs or light sources (not shown), which may be used to image the end effector of the instrument deployed from the sheath and/or otherwise image a surgical field during a procedure. One or more processors may be coupled to the imaging elements for activating the elements, acquiring images or other signals, and/or for providing output signals to a display, which may be observed by the surgeon during use. For example, a display may be mounted on or otherwise carried on the proximal end of the device, e.g., on the handle 41 of the devices 20, 120 shown in FIG. 5 or 8*a*, on the proximal end of the sheath 115 shown in FIG. 8*a*, on the frame 236 shown in FIG. 11*a*, or separate from the devices or systems, e.g., included in the control console 340 shown in FIG. 13*a*.

Figure 16:
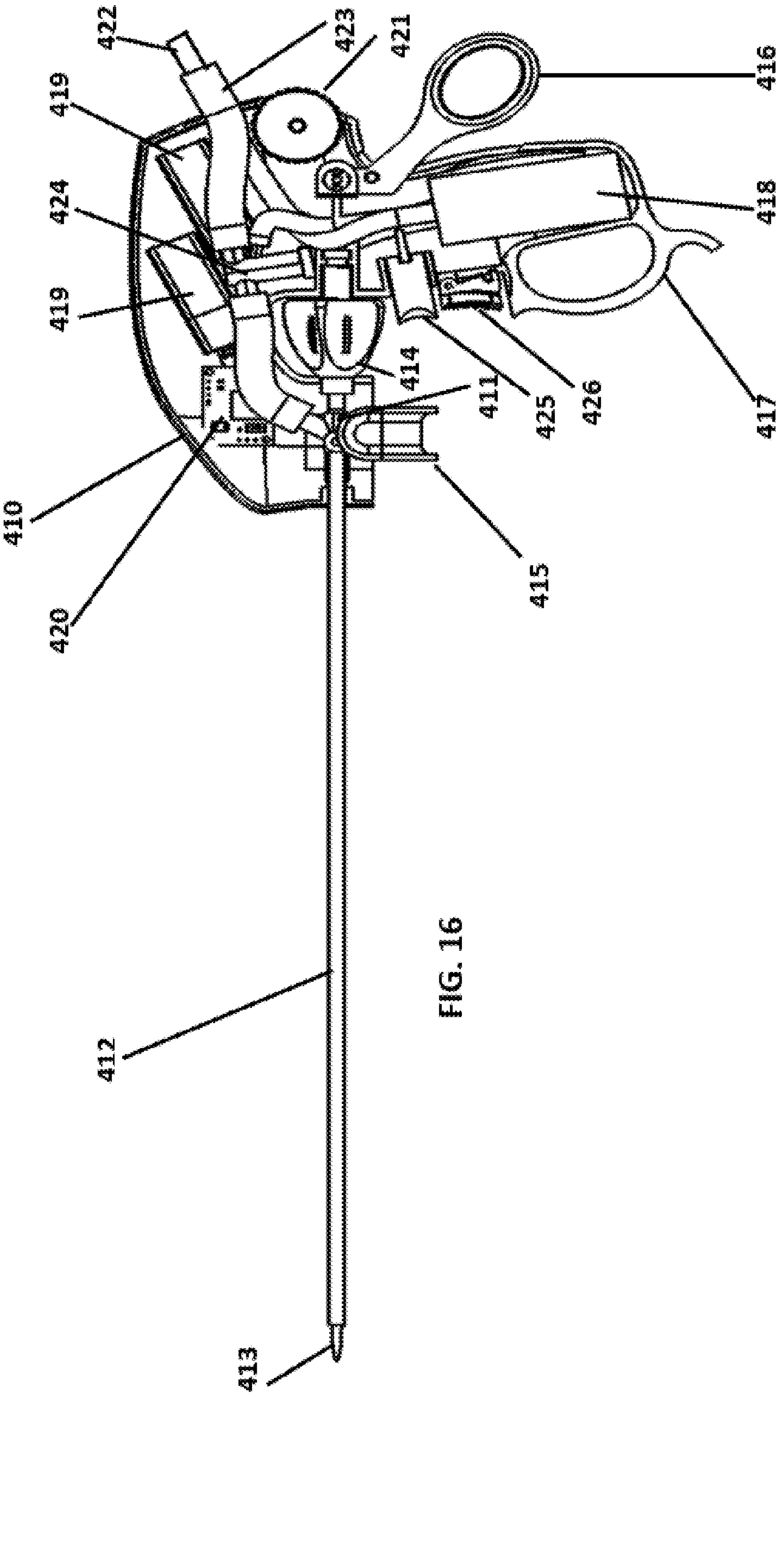
FIG. 16 illustrates the layout of the components included in an exemplary hydro dissection, irrigation, and suction laparoscopic forceps device.

Turning to FIG. 16 another example of a laparoscopic forceps device 410 is shown that may selectively be operated to perform hydro dissection, irrigation, and suction. In the example shown, the shaft 411 of a three-millimeter (3 mm) diameter laparoscopic forceps lie within the length of a five millimeter (5 mm) diameter outer sheath 412, and jaws 413 of the laparoscopic forceps extend distal to the tip of the outer sheath 412. An actuation knob 414 allows the surgeon to rotate the shaft 411 and jaws 413 of the forceps. The outer sheath 412 may be advanced distally to completely cover the forceps jaws 413, e.g., by axial displacement of sheath actuator 415. Forceps jaws 413 are opened and closed via thumb manipulation of a movable ring or other actuator 416, while the stationary loop 417 accommodates the user's third and fourth fingers.

The inner components of the device 410 may be observed in this opened view of the handle housing, i.e., with a cover of the handle removed. An electric fluid pump 418 provides a pressurized source of saline fluid. Electric power is supplied to the pump 418 via two nine-volt batteries 419 or other power source, with an electronic board 420 maintaining a constant voltage source. An externally accessible control 421 to a potentiometer may be provided to allow the surgeon to vary the voltage input to the pump 418, e.g., to increase or decrease the velocity of the fluid emitted by the device. Fluid input connector 422 accepts an intravenous line connected to a saline bag that is elevated, e.g., approximately one meter above the level of the patient on the operating table. The elevated saline bag provides an additional pressure head supply to the fluid pump 418 to increase the flow velocity of the fluid jet used for surgical hydro dissection. A separate suction connector 423 may be attached to a vacuum line that connects to a standard operating room vacuum source.

Delivery of either fluid flow or vacuum to outer sheath 412 is governed by a mechanical valve 424. Fluid control switch 425 is a spring loaded electrical On/Off switch that powers fluid pump 418. Suction control switch 426 is a mechanical switch that selects vacuum as the mode supplied to outer sheath 412.

FIG. 17*a* depicts the configuration of the controls in the device 410 when the device 410 is supplying fluid in a low velocity fluid irrigation/suction mode. The sheath actuator 415 is moved forward to achieve full distal advancement of the outer sheath 412. A flexible fluid line 427 accommodates forward motion of the actuator 415 to transfer fluid from stationary valve 424 to moveable outer sheath 412. FIG. 17*b* illustrates the device configuration upon full distal advancement of outer sheath 412. A bushing 428 attached to distal end of outer sheath 412 completely covers laparoscopic forceps jaws 413. Since the jaws 413 exhibit a distally tapering profile, a large fluid flow path 430 exists between the outer profile of jaws 413 and the inner diameter in the opening in the end cap on bushing 428. This results in low velocity irrigation exiting the outer sheath 412.

FIG. 17*c* depicts retraction of the outer sheath 412 by backward movement of the sheath actuator 415, i.e., to configure the device in a hydro-dissection mode. FIG. 17*d* illustrates the resultant position of the distal end of the device 410, with the forceps jaws 413 fully exposed and functional in opening and closing. The end cap on the distal bushing 428 lies in contact with the shaft of the laparoscopic forceps, preventing circumferential fluid flow from exiting around the periphery of the forceps jaws 413, and forcing all fluid flow to exit through the small diameter nozzle 429 in the end cap of the distal bushing 428, thus forming a high velocity hydro dissection fluid jet 431. FIG. 17*e* is a sectional view with an arrow illustrating the resultant fluid path taken during high velocity hydro dissection, as the forceps jaws 413 close off the annular opening in the end cap of the bushing 428 and forces all fluid flow to exit the small diameter nozzle 429. Bushing 428 is constructed of a rigid, non-conductive material able to withstand elevated temperatures exhibited by application of radiofrequency energy to forceps jaws 413 during tissue cautery. Anodized aluminum may be used, as it contains all of the foregoing features.

Figure 18A:
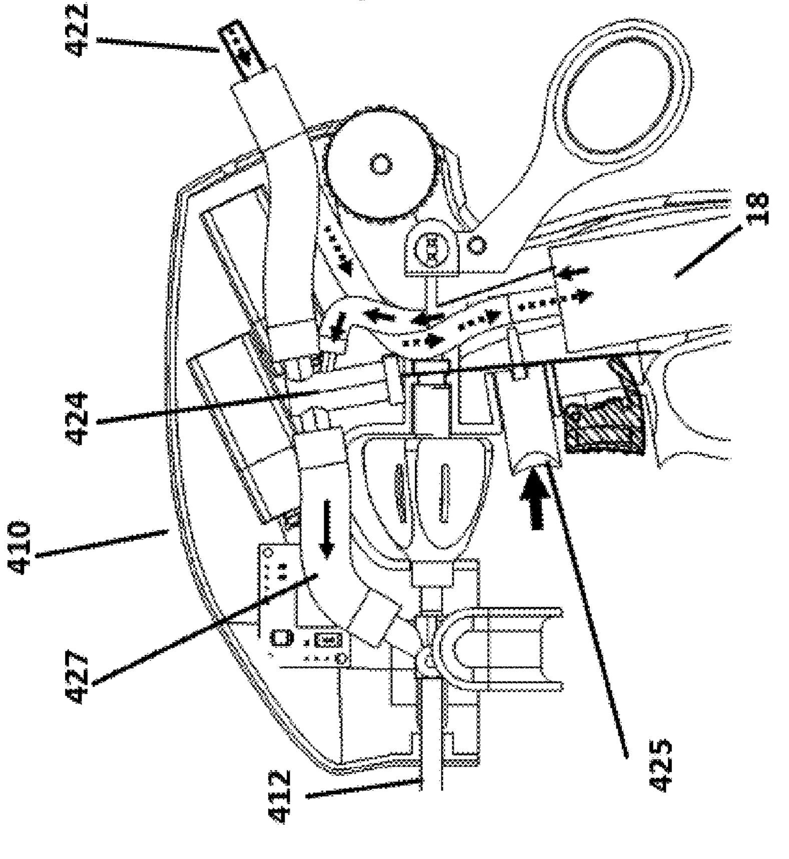
FIG. 18*a*-18*b* show control button activation of fluid flow and suction modes for the device.
Figure 18B:
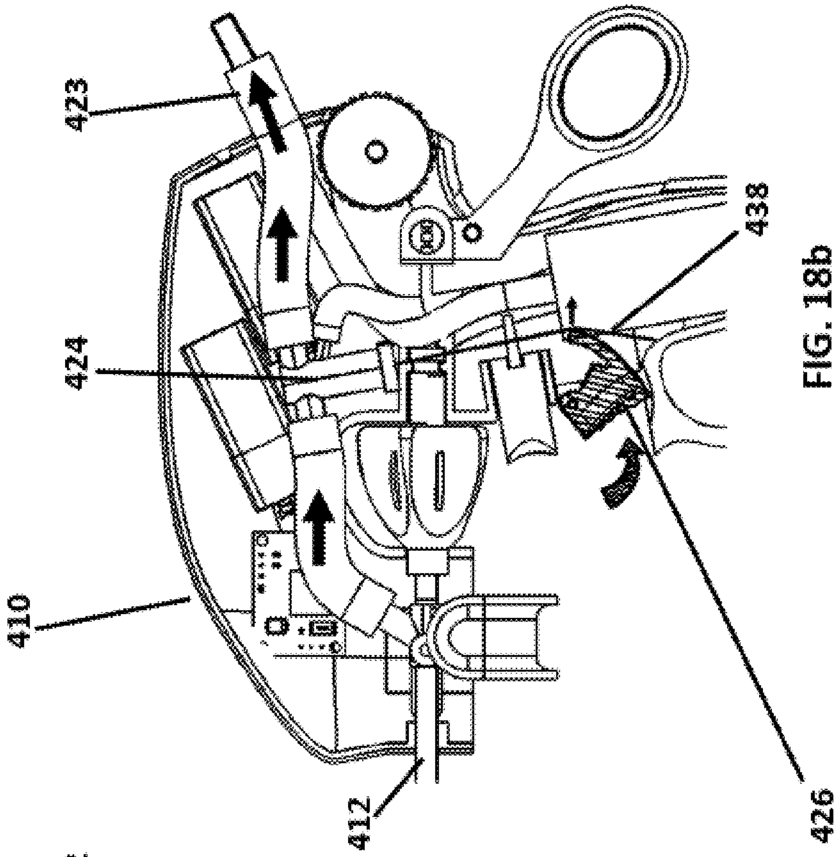

FIG. 18*a* illustrates activation of fluid flow in the device 410. Button switch 425 is depressed to activate electrical fluid pump 418, causing fluid to flow into the pump 418 via fluid input connector 422, as illustrated by the dashed arrows. Fluid output from the pump 418, as illustrated by the solid arrows, enters valve 424, proceeds through flexible fluid line 427, and continues through the lumen of the sheath 414. FIG. 18*b* illustrates activation of suction in the device 410. Depression of suction button 426 exerts traction on the inelastic cable 439 that actuates valve 424, simultaneously cutting off antegrade fluid flow while enabling retrograde suction to occur. The solid arrows illustrate the path of suction flow in a retrograde manner from the lumen of outer sheath 414 through valve 424 to the suction connector 423.

Figure 19B:
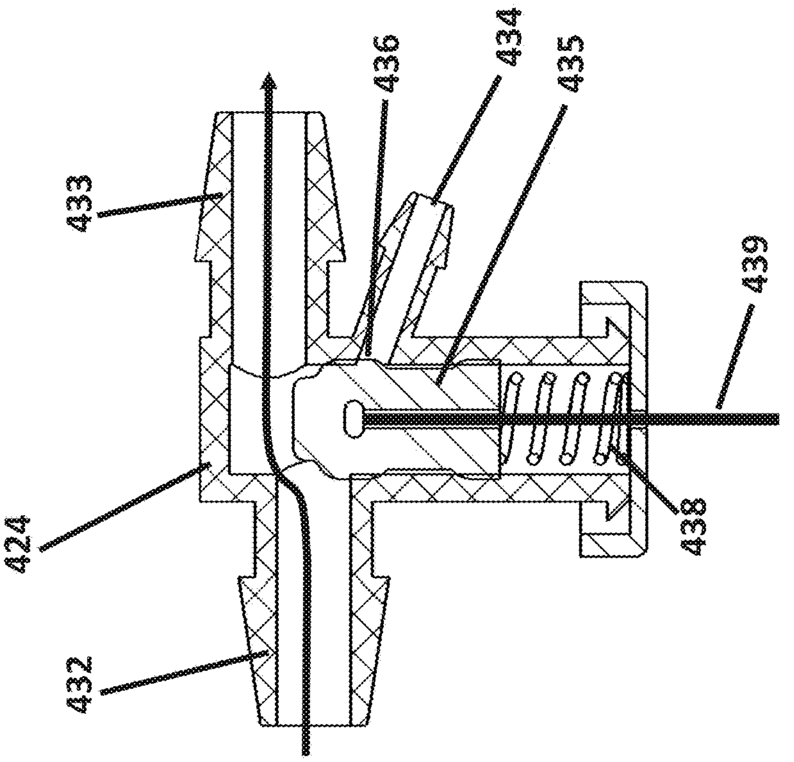
FIGS. 19*a*-19*b* depicts the two configurations of the specialized valve that selects for either fluid flow or suction via the distal tip of the device.
Figure 19A:
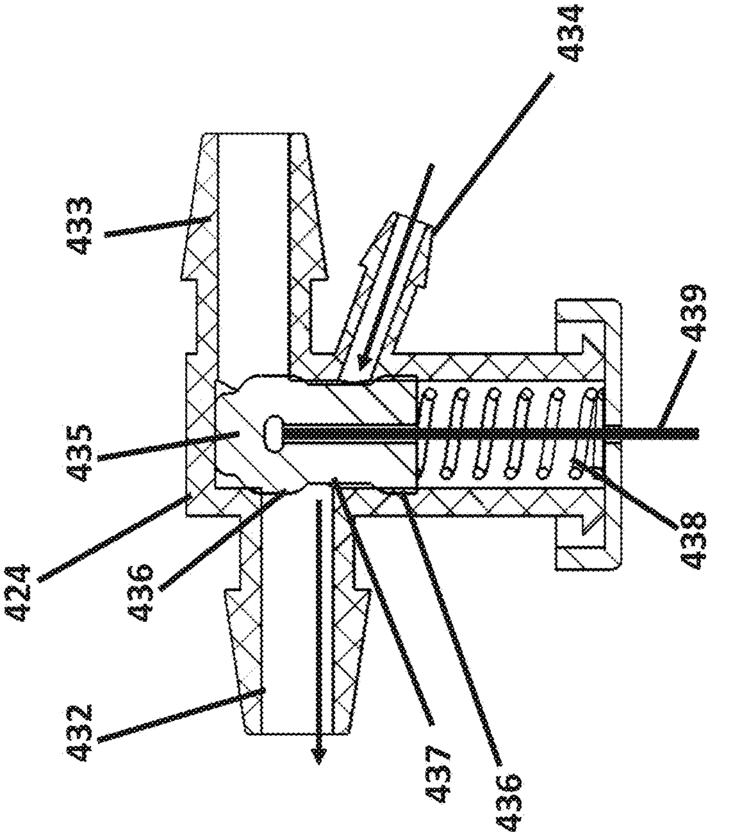

FIG. 19*a* depicts the fluid and suction control valve 424 in its normal resting position, in which suction is cut off, but fluid flow is enabled. The valve stem 435 contains an hourglass shape, with wide portions 436 and a central narrow portion 437. Compression spring 438 exerts force on valve stem 435, displacing it superiorly such that the enlarged portion 436 completely obstructs vacuum flow between valve outlet port 432 and suction inlet port 433.

In the resting position, the narrow valve stem portion 437 is aligned with fluid intake port 434 and valve outlet port 432, enabling fluid flow to occur through the control valve 424. In the normal resting position of valve 424, no tension is exerted on valve stem 435 by the attached inelastic cable 439. In one example, the valve stem 435 may be constructed of an inelastic polymer such as Nylon, polyethylene, or polytetrafluoroethylene (PTFE); or it may be constructed of a partially elastic polymer such as polyurethane.

FIG. 19*b* depicts control valve 424 activated to supply suction while cutting off fluid flow. Upon exertion of traction to the cable 439, the spring 438 is compressed and the valve stem 435 is pulled into position whereby it occludes fluid flow from the fluid intake port 434 while opening a path from the suction intake port 433 to the valve outlet port 432.

Figure 20C:
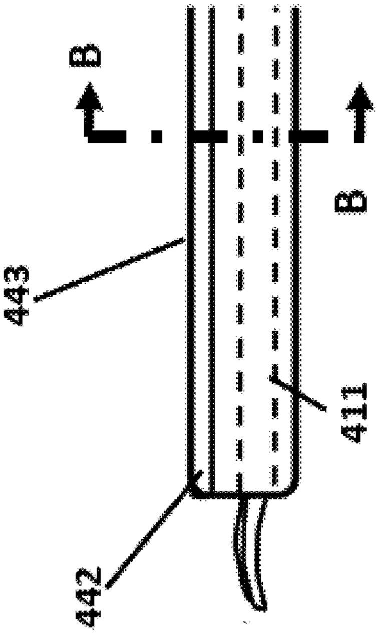
FIGS. 20*a*-20*d* illustrates the difference in effective vacuum flow area between the current device and the previous device containing a full-length fluid jet channel.
Figure 20D:
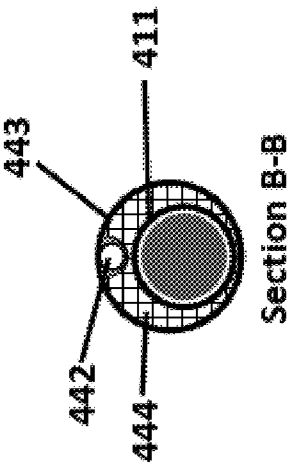
Figure 20A:
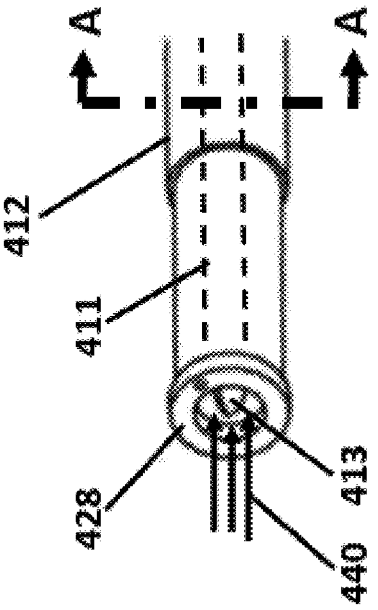
Figure 20B:
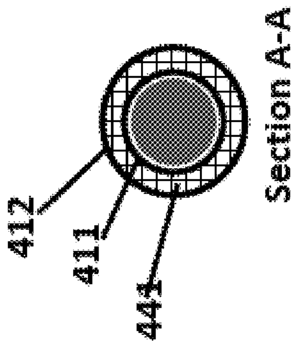

FIG. 20*a* shows the distal portion of the device 410 in the suction configuration, with the dotted outline representing the shaft of the laparoscopic forceps 411 inside the outer sheath 412. Suction airflow 440 occurs in the annular space between the forceps jaws 412 and the opening in the end cap of the bushing 428. FIG. 20*b* is a sectional view of the instrument shaft at A-A, with the cross-hatched region 441 depicting the suction flow path area between the instrument shaft 411 and the outer sheath 412.

FIG. 20*c* shows the distal portion of a previous device described in one of the applications incorporated by reference herein, with a small diameter stainless steel tube 442 welded to the inner aspect of outer tube 443. The dotted outline represents the shaft of the laparoscopic forceps 411 inside the outer tube 443. FIG. 20*d* is a sectional view of the instrument shaft at B-B, with the cross-hatched region 444 depicting the suction flow path area between the instrument shaft 411 and the contours of the jet flow tube 442 and the outer tube 443, for an instrument with the previous configuration. Calculations show that the cross-sectional suction flow area 444 of the previous device is 22.2% less than the effective flow area 441 of the proposed device. This suction capability will be significant during clinical use, when blood clots and debris are encountered during suction use.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for performing a surgical procedure within a patient's body, comprising:

an outer sheath comprising a proximal end, a distal end, and a lumen extending between the proximal and distal ends;

an instrument comprising a shaft, an end effector on a distal end of the shaft extending distally from the sheath distal end, the shaft sized to accommodate fluid flowing through the lumen around the shaft;

a tubular member slidable on the sheath distal end between a distal position in which a primary passage in a distal tip of the tubular member is disposed distally beyond the sheath distal end and a proximal position in which the tubular member seals against the shaft to prevent flow through the primary passage, the tubular member comprising a secondary lumen extending through the distal tip adjacent the primary passage, the secondary passage having a cross-section smaller than the cross-section of the primary passage;

a handle on the proximal end of the sheath comprising a first actuator coupled to the tubular member to move the tubular member between the distal and proximal positions; and a source of fluid coupled to the lumen to deliver pressurized fluid through the lumen and out an outlet in the sheath distal end to dissect tissue such that, in the distal position, the fluid flows through the lumen around the shaft and out the primary passage to provide irrigation fluid, and, in the proximal position, the fluid flows through the lumen and out the secondary passage to provide hydro-dissection fluid.

2. The device of claim 1, further comprising a second actuator on the handle for actuating the end effector.

3. The device of claim 2, wherein the end effector comprises a pair of jaws coupled to the second actuator for directing the jaws between open and closed positions.

4. The device of claim 3, wherein the jaws comprise substantially blunt contact surfaces configured to grasp tissue between the jaws in the closed position.

5. The device of claim 4, further comprising a third actuator on the handle configured to activate the source of fluid after the jaws grasp tissue to deliver the pressurized fluid through the lumen with the tubular member in the proximal position to perform hydro-dissection.

6. The device of claim 1, wherein the source of fluid comprises a pump carried by the handle.

7. The device of claim 6, wherein the source of fluid further comprises a reservoir of fluid coupled to the pump.

8. The device of claim 1, further comprising:

a connector on the handle configured to be coupled to a source of suction;

a valve in a flow path between the connector and the lumen; and an actuator for selectively operating the valve to selectively open and close the flow path and deliver suction via the lumen and the primary passage with the tubular member in the distal position.

9. The device of claim 1, further comprising a cautery element on the end effector, the handle comprising a connector for coupling the cautery element to a source of energy to deliver energy to the cautery element to cauterize tissue contacted by the cautery element.

10. The device of claim 9, wherein the cautery element comprises one or more electrodes on the end effector.

11. The device of claim 9, wherein the end effector comprises a pair of jaws and wherein the cautery element comprises one of a conductive surface and an electrode on one of the jaws.

12. The device of claim 9, wherein the source of energy comprises a generator configured to be coupled to the connector to deliver electrical energy to the cautery element via one or more leads to cauterize tissue contacted by the cautery element.

* * * * *